(12) United States Patent
Kitagawa et al.

(10) Patent No.: US 9,750,477 B2
(45) Date of Patent: Sep. 5, 2017

(54) RADIATION IMAGING SYSTEM AND OPERATING METHOD THEREOF, AND RADIATION IMAGE DETECTING DEVICE

(71) Applicant: FUJIFILM Corporation, Tokyo (JP)

(72) Inventors: Yusuke Kitagawa, Ashigarakami-gun (JP); Takashi Tajima, Ashigarakami-gun (JP); Keita Watanabe, Ashigarakami-gun (JP); Takeshi Kamiya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 596 days.

(21) Appl. No.: 14/225,762

(22) Filed: Mar. 26, 2014

(65) Prior Publication Data

US 2014/0205066 A1  Jul. 24, 2014

Related U.S. Application Data

(63) Continuation of application No. PCT/JP2012/073061, filed on Sep. 10, 2012.

(30) Foreign Application Priority Data

Sep. 27, 2011 (JP) .................. 2011-210147
Dec. 27, 2011 (JP) .................. 2011-285738

(51) Int. Cl.
 *H04N 5/32* (2006.01)
 *A61B 6/00* (2006.01)
 (Continued)

(52) U.S. Cl.
 CPC ............ *A61B 6/542* (2013.01); *A61B 6/5241* (2013.01); *G01T 1/2018* (2013.01); *H04N 5/32* (2013.01);
 (Continued)

(58) Field of Classification Search
 CPC .. A61B 6/025; A61B 6/06; A61B 6/08; A61B 6/4233; A61B 6/4283; A61B 6/505;
 (Continued)

(56) References Cited

U.S. PATENT DOCUMENTS 6,208,710 B1   3/2001  Nagai
6,797,960 B1   9/2004  Spartiotis et al.
(Continued)

FOREIGN PATENT DOCUMENTS

EP   1 001 665 A2   5/2000
JP   09-055298 A    2/1997
(Continued)

OTHER PUBLICATIONS

PTO 113916 which is a translation of JP 2007-215918A.*
(Continued)

*Primary Examiner* — David J Makiya
*Assistant Examiner* — John Corbett
(74) *Attorney, Agent, or Firm* — Birch, Stewart, Kolasch & Birch, LLP

(57) ABSTRACT

A measurement area selection circuit has an irradiation field determination unit, an object area determination unit, and a measurement area determination unit. The irradiation field determination unit determines an irradiation field of an imaging surface of an FPD. The object area determination unit determines an object area from a comparison result between a first expected received dose of a directly exposed area and dose detection signals of detection pixels situated in the irradiation field. The measurement area determination unit determines a measurement area, which corresponds to a region of interest, from a comparison result between a second expected received dose of the measurement area and the dose detection signals of the detection pixels situated in the irradiation area and the object area. The dose detection (Continued)

signals of the detection pixels situated in the measurement area are used for AEC.

18 Claims, 18 Drawing Sheets

(51) Int. Cl.
  *G01T 1/20* (2006.01)
  *G03B 42/02* (2006.01)
  *A61B 6/02* (2006.01)
  *A61B 6/06* (2006.01)
  *A61B 6/08* (2006.01)
(52) U.S. Cl.
  CPC ............... *A61B 6/025* (2013.01); *A61B 6/06* (2013.01); *A61B 6/08* (2013.01); *A61B 6/4233* (2013.01); *A61B 6/4283* (2013.01); *A61B 6/505* (2013.01); *A61B 6/547* (2013.01); *G03B 42/02* (2013.01)
(58) Field of Classification Search
  CPC ....... A61B 6/5241; A61B 6/542; A61B 6/547; G01T 1/2018; G03B 42/02; H04N 5/32
  See application file for complete search history.

(56) References Cited

U.S. PATENT DOCUMENTS

| | | | |
|---|---|---|---|
| 7,734,013 | B2 | 6/2010 | Kashiwagi et al. |
| 2004/0028182 | A1 | 2/2004 | Tamegai |
| 2004/0149920 | A1 | 8/2004 | Ishii et al. |
| 2004/0234032 | A1 | 11/2004 | Nokita |
| 2009/0087073 | A1* | 4/2009 | Kito .................. A61B 6/00 382/132 |
| 2011/0075810 | A1 | 3/2011 | Sendai |
| 2011/0180717 | A1* | 7/2011 | Okada .................... H04N 5/374 250/370.08 |
| 2011/0249791 | A1* | 10/2011 | Wang ....................... A61B 6/08 378/62 |

FOREIGN PATENT DOCUMENTS

| | | | |
|---|---|---|---|
| JP | 2000-037372 A | | 2/2000 |
| JP | 2002-543684 A | | 12/2002 |
| JP | 2004-069441 A | | 3/2004 |
| JP | 2004-251892 A | | 9/2004 |
| JP | 2004-344249 A | | 12/2004 |
| JP | 2005-143802 A | | 6/2005 |
| JP | 2007215918 A | * | 8/2007 |
| JP | 2007-229363 A | | 9/2007 |
| JP | 2007-259932 A | | 10/2007 |
| JP | 2008-245991 A | | 10/2008 |
| JP | 2009-291356 A | | 12/2009 |
| JP | 2010-214056 A | | 9/2010 |
| JP | 2011-010870 A | | 1/2011 |
| JP | 2011-067321 A | | 4/2011 |
| JP | 2011-067333 A | | 4/2011 |
| JP | 2011-115368 A | | 6/2011 |
| JP | 2011-174908 A | | 9/2011 |
| JP | 2011-183006 A | | 9/2011 |
| WO | WO 2009/142166 A1 | | 11/2009 |

OTHER PUBLICATIONS

PTO 16-113736 which is a translation of JP 2008-245991 A.*
Japanese Office Action, dated Jul. 8, 2015, for Japanese Application No. 2013-536138, with an English translation.
International Search Report for PCT/JP2012/073061 dated Nov. 27, 2012.
EnglishTranslations of the International Preliminary Report on Patentability and Written Opinion of the International Searching Authority (Forms PCT/IB/338, PCT/IB/373, PCT/ISA/237), dated Apr. 10, 2014, for International Application No. PCT/JP2012/073061.
Japanese Office Action, dated Jan. 4, 2017, for Japanese Application No. 2016-037008, full translation supplied.

* cited by examiner

| BODY PART | TUBE VOLTAGE (kV) | TUBE CURRENT (mA) | SECOND EXPECTED RECEIVED DOSE | EMISSION STOP THRESHOLD VALUE |
|---|---|---|---|---|
| ⋮ | ⋮ | ⋮ | ⋮ | ⋮ |
| CHEST | V1 | I1 | E1 | TH1 |
| HEAD | V2 | I2 | E2 | TH2 |
| ⋮ | ⋮ | ⋮ | ⋮ | ⋮ |

RADIATION IMAGING SYSTEM AND OPERATING METHOD THEREOF, AND RADIATION IMAGE DETECTING DEVICE

This application is a Continuation of PCT/JP2012/073061 filed on Sep. 10, 2012, which claims priority under 35 U.S.C. 119(a) to Patent Application Nos. 2011-210147 filed on Sep. 27, 2011 in Japan and 2011-285738 filed on Dec. 27, 2011 in Japan, all which are hereby expressly incorporated by reference into the present application.

BACKGROUND OF THE INVENTION

1. Field of the Invention

The present invention relates to a radiation imaging system and an operating method thereof, and a radiation image detecting device.

2. Description Related to the Prior Art

In a medical field, an X-ray imaging system using X-rays, as a kind of radiation, is known. The X-ray imaging system is constituted of an X-ray generating apparatus for generating the X-rays and an X-ray imaging apparatus, which receives the X-rays and takes an X-ray image. The X-ray generating apparatus includes an X-ray source for emitting the X-rays to an object, a source control device for controlling the operation of the X-ray source, and an emission switch for inputting an emission start command of the X-rays. The X-ray imaging apparatus includes an X-ray image detecting device, which detects the X-ray image upon receiving the X-rays passed through the object, and a console, which controls the operation of the X-ray image detecting device and applies various types of image processes to the X-ray image.

Recently, in a field of the X-ray imaging system, an X-ray image detecting device that uses a flat panel detector (FPD) as a detection panel, instead of an X-ray film or an imaging plate (IP), becomes widespread. The FPD has a matrix of pixels each for accumulating signal charge in accordance with the amount of X-rays incident thereon. The FPD accumulates the signal charge on a pixel-by-pixel basis. The FPD converts the accumulated signal charge into a voltage signal at its signal processing circuit, and thereby detects the X-ray image representing image information of the object and outputs the X-ray image as digital image data.

An electronic cassette (portable X-ray image detecting device) that is composed of the FPD contained in a rectangular parallelepiped housing is in practical use. The electronic cassette is used while being loaded detachably into an existing imaging stand sharable with a film cassette and an IP cassette or a specific imaging stand designed for the electronic cassette, in contrast to a non-detachable type. Furthermore, the electronic cassette is used while being put on a bed or held by the object himself/herself, to take an image of a body part that is hard to take with the non-detachable type. The electronic cassette is sometimes brought out from a hospital to a place having no imaging stand, for use in bedside radiography of an elder patient or in urgent radiography of an injured patient, natural disaster victims, or the like.

Also, for the purpose of obtaining a radiographic image of appropriate image quality with reducing radiation exposure of the object, the X-ray imaging system sometimes performs automatic exposure control (AEC) in which an integrated value (accumulative dose) of an X-ray dose is measured during exposure to (irradiation with) the X-rays and X-ray emission from the X-ray source is stopped as soon as the accumulative dose has reached a target value. The X-ray dose applied by the X-ray source is determined by a tube current-emission time product (mAs value), being a product of an emission time (in seconds) of the X-rays and a tube current (in mA) for defining the X-ray dose applied per unit of time by the X-ray source. Although imaging conditions, including the emission time and the tube current, have approximate recommended values in accordance with a body part (chest or head) to be imaged, sex, age, and the like of the object, X-ray transmittance varies depending on the individual difference such as physique of the object. Therefore, the automatic exposure control is carried out in order to obtain more appropriate image quality.

In carrying out the automatic exposure control, the X-ray imaging system is provided with a dose detection sensor for detecting the X-ray dose passed through the object. If there are provided a plurality of dose detection sensors, a measurement area (radiation dose measurement area) that corresponds to an area (also called a region of interest or a ROI) that is the most noteworthy in making a diagnosis is set in accordance with a body part to be imaged. The timing of stopping the X-ray emission is judged based on the X-ray dose detected by the dose detection sensor disposed in the measurement area.

According to U.S. Pat. No. 7,734,013, the dose detection sensor that is disposed in a position corresponding to a mammary gland, being the measurement area, is extracted based on output of the plurality of dose detection sensors (AEC sensors) in pre-exposure, to use the extracted dose detection sensor as a sensor in actual exposure. The position of the mammary gland is determined using an average of output of the dose detection sensors.

European Patent Publication No. 1001665 A2 discloses a radiation imaging system that uses signal lines (data lines) of pixels in the AEC. The signal line of the pixels corresponding to the measurement area is automatically chosen with a program.

According to Japanese Patent Application Publication No. 09-055298, a non-irradiation field, a directly exposed area (directly irradiation field), and the measurement area (irradiation field of the object) are recognized by a histogram analysis of pixel values of a radiographic image. A dose detection sensor (imaging sensor) corresponding to the measurement area is chosen by comparison with a typical value of a pixel in the measurement area.

According to Japanese Patent Application Publication No. 2005-476802, in a radiation image reading device using a CMOS image sensor, a stop of the X-ray emission is judged based on a signal of a pixel having the highest signal value (in the directly exposed area), out of all pixels of the CMOS image sensor.

In setting the measurement area, requiring the pre-exposure as described in the U.S. Pat. No. 7,734,013 or the histogram analysis as described in the Japanese Patent Application Publication No. 09-055298 causes complication of a process and increase in time of the process. Also there is a problem that the pre-exposure or radiography poses unnecessary exposure of the patient.

In the European Patent Publication No. 1001665 A2, the data line of the pixels corresponding to the measurement area is automatically chosen, but it does not describe how to choose the data line. The Japanese Patent Application Publication No. 2005-143802 is aims at judging an end of the X-ray emission, and is unsuitable for the AEC for judging when to stop the X-ray emission.

SUMMARY OF THE INVENTION

An object of the present invention is to provide a radiation imaging system and an operating method thereof, and a radiation image detecting device that can set the AEC measurement area easily and speedily.

A radiation imaging system according to the present invention includes a radiation source for emitting radiation to an object, and a radiation image detecting device having a detection panel formed with an imaging surface for imaging a radiographic image of the object. The imaging surface has an array of a plurality of pixels each for accumulating electric charge in accordance with a received dose of the radiation emitted from the radiation source. The radiation imaging system includes a plurality of dose detection sensor, an expected received dose obtainment unit, an area determination unit, and an automatic exposure control unit. The plurality of dose detection sensors are disposed in the imaging surface, for detecting the received dose. The expected received dose obtainment unit obtains an expected received dose that is expected to be applied to a part of the imaging surface. The area determination unit determines a measurement area out of the imaging surface based on a comparison result between the expected received dose and the received dose detected by the dose detection sensor. The measurement area is used in performing automatic exposure control that makes the radiation source stop emitting the radiation to control exposure of the radiographic image. The automatic exposure control unit performs the automatic exposure control based on a comparison result between an integrated value of the received dose detected by the dose detection sensor situated in the measurement area and a predetermined emission stop threshold value.

The expected received dose obtainment unit preferably calculates a first expected received dose of a directly exposed area in which the radiation is directly applied to the imaging surface without passing through the object, based on a distance between the radiation source and the imaging surface of the radiation image detecting device and tube voltage and tube current applied to the radiation source. The area determination unit preferably determines the directly exposed area by a comparison result between the first expected received dose and the received dose detected by the dose detection sensor, and determines an object area to which the radiation is applied through the object based on the determined directly exposed area.

The expected received dose obtainment unit preferably calculates the first expected received dose by using an area dose expression by a NDD method.

The measurement area is preferably an area set at a region of interest being most noteworthy in making a diagnosis. The radiation imaging system preferably includes an operation input unit for designating a body part to be imaged, and a memory unit for storing a second expected received dose that is expected to be received by the measurement area on a body part basis. The expected received dose obtainment unit preferably obtains from the memory unit the second expected received dose in accordance with the body part inputted by the operation input unit. The area determination unit preferably determines the measurement area from a comparison result between the second expected received dose and the received dose detected by the dose detection sensor.

The radiation image detecting device preferably includes a gain variable amplifier and a gain setting unit. The gain variable amplifier amplifies an analog voltage signal that corresponds to electric charge from the pixel in a readout operation for reading out the radiographic image from the detection panel. The gain setting unit sets a gain of the amplifier during the readout operation, based on the received dose detected by the dose detection sensor situated in the measurement area in the automatic exposure control.

The area determination unit may perform area determination by comparing with the expected received dose a typical value of the received doses detected by a plurality of the dose detection sensors contained in a block into which the imaging surface is divided.

The measurement area is preferably an area set at a region of interest that is most noteworthy in making a diagnosis. The radiation imaging system preferably includes a candidate area setting unit for setting a candidate area of the measurement area. The area determination unit preferably determines the measurement area out of the candidate area.

The radiation source is preferably provided with an irradiation field limiter for limiting an irradiation field that is irradiated with the radiation within the imaging surface. The radiation imaging system preferably includes an irradiation field determination unit for determining the irradiation field in the imaging surface based on a collimator angle of the irradiation field limiter and the positional relation between the radiation source and the radiation image detecting device.

It is preferable that the irradiation field determination unit determines the irradiation field, and then the area determination unit determines the object area in the irradiation field and then determines the measurement area in the object area.

The measurement area is preferably an area set at a region of interest that is most noteworthy in making a diagnosis. The radiation imaging system preferably includes a candidate area setting unit for setting a candidate area of the measurement area. The irradiation field determination unit preferably determines the irradiation field out of the candidate area.

The area determination unit may perform area determination immediately after the radiation source starts emitting the radiation and in a period when the received dose is increasing. Otherwise, the area determination unit may perform the area determination after the radiation source starts emitting the radiation and the received dose comes to a constant value.

The automatic exposure control unit preferably makes the radiation source stop emitting the radiation, as soon as the integrated value has reached the emission stop threshold value. The automatic exposure control unit may calculate an expected time required for the integrated value to reach the emission stop threshold value, and make the radiation source stop emitting the radiation after a lapse of the calculated time.

In an operating method of a radiation imaging system according to the present invention, the radiation imaging system includes an automatic exposure control unit for performing automatic exposure control by which emission of the radiation from the radiation source is stopped based on a comparison result between an integrated value of the received dose detected by the dose detection sensor and a predetermined emission stop threshold value in order to control exposure of the radiographic image. The operating method includes an expected received dose obtaining step, an area determining step, and an automatic exposure controlling step. In the expected received dose obtaining step, an expected received dose that is expected to be applied to a part of the imaging surface is obtained. In the area determining step, a measurement area used in performing the automatic exposure control is determined out of the imaging surface based on a comparison result between the expected received dose and the received dose detected by the dose detection sensor. In the automatic exposure controlling step, the automatic exposure control is performed by using the dose detection sensor situated in the measurement area.

A radiation image detecting device according to the present invention includes a detection panel, a plurality of dose detection sensors, an expected received dose obtainment unit, an area determination unit, and an automatic exposure control unit. The detection panel is formed with an imaging surface for imaging a radiographic image of an object. The imaging surface has an array of a plurality of pixels each for accumulating electric charge in accordance with a received dose of radiation emitted from a radiation source. The dose detection sensors are disposed in the imaging surface, for detecting the received dose. The expected received dose obtainment unit obtains an expected received dose that is expected to be applied to a part of the imaging surface. The area determination unit determines a measurement area out of the imaging surface based on a comparison result between the expected received dose and the received dose detected by the dose detection sensor. The measurement area is used in performing automatic exposure control that makes the radiation source stop emitting the radiation to control exposure of the radiographic image. The automatic exposure control is performed based on a comparison result between an integrated value of the received dose detected by the dose detection sensor situated in the measurement area and a predetermined emission stop threshold value.

According to the present invention, the expected received dose that is expected to be received by a part of the imaging surface is obtained, and the measurement area used in performing the automatic exposure control is determined from a comparison result between the expected received dose and the received dose detected by the dose detection sensor. Therefore, it is possible to provide a radiation imaging system that can easily and speedily set the AEC measurement area, an operating method of the radiation imaging system, and a radiation image detecting device.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

First Embodiment

Figure 1:
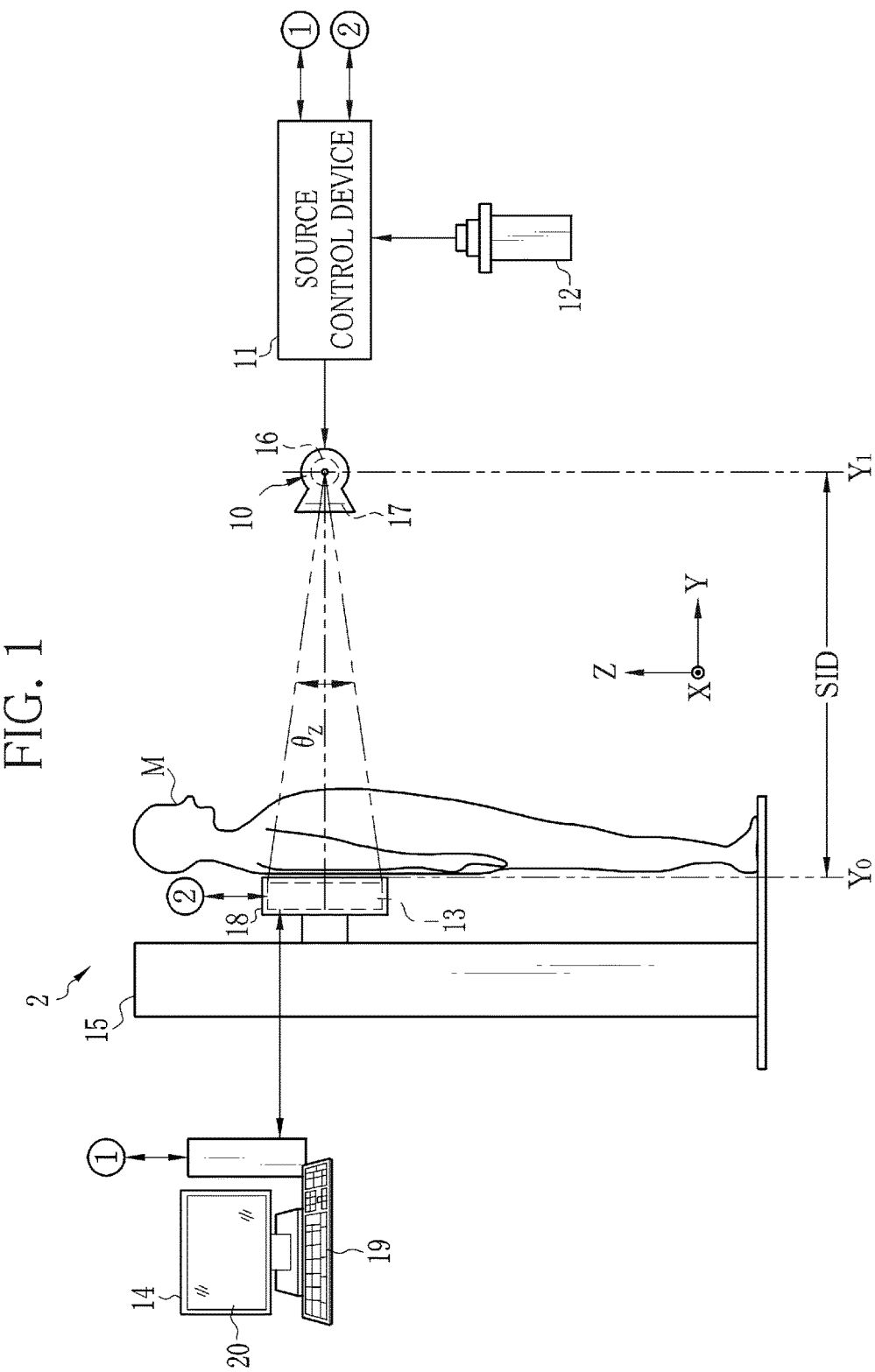
FIG. 1 is a schematic view showing the structure of an X-ray imaging system.

In FIG. 1, an X-ray imaging system 2 is constituted of an X-ray source 10, a source control device 11 for controlling the operation of the X-ray source 10, an emission switch 12 for commanding a start of X-ray emission, an electronic cassette 13 for detecting X-rays passed through an object M and outputting an X-ray image, a console 14 for controlling the operation of the electronic cassette 13 and applying an image process to the X-ray image, and an imaging stand 15 for imaging the object M in a standing position. The X-ray source 10, the source control device 11, and the emission switch 12 compose an X-ray generating apparatus. The electronic cassette 13 and the console 14 compose an X-ray imaging apparatus. Additionally, an imaging table for imaging the object M in a lying position, a source shift mechanism for setting the X-ray source 10 in a desired orientation and position, and the like are provided.

The X-ray source 10 has an X-ray tube 16 for radiating the X-rays and an irradiation field limiter (collimator) 17 for limiting an irradiation field of the X-rays radiating from the X-ray tube 16 to a rectangular shape. The X-ray tube 16 has a cathode composed of a filament for emitting thermoelectrons, and an anode (target) that radiates the X-rays by collision of the thermoelectrons emitted from the cathode. The irradiation field limiter 17 is composed of, for example, four lead plates for blocking the X-rays. The four lead plates are disposed in each side of a rectangle so as to form a rectangular irradiation opening in a middle to pass the X-rays therethrough. Under the control of the source control device 11, shifting the position of the lead plates varies the size of the irradiation opening to limit the irradiation field.

The source control device 11 adjusts an angle range (hereinafter called collimator angle) of the X-rays radiating from the irradiation field limiter 17 in two directions, that is, a Z direction perpendicular to a floor of an examination room and an X direction (perpendicular to the drawing) being a width direction of an imaging surface 47 of an FPD 45 (both see FIG. 3) of the electronic cassette 13, such that the irradiation field of the X-rays almost coincides with the imaging surface 47. In the drawing, "$\theta_Z$" represents the collimator angle with respect to the Z direction.

Figure 2:
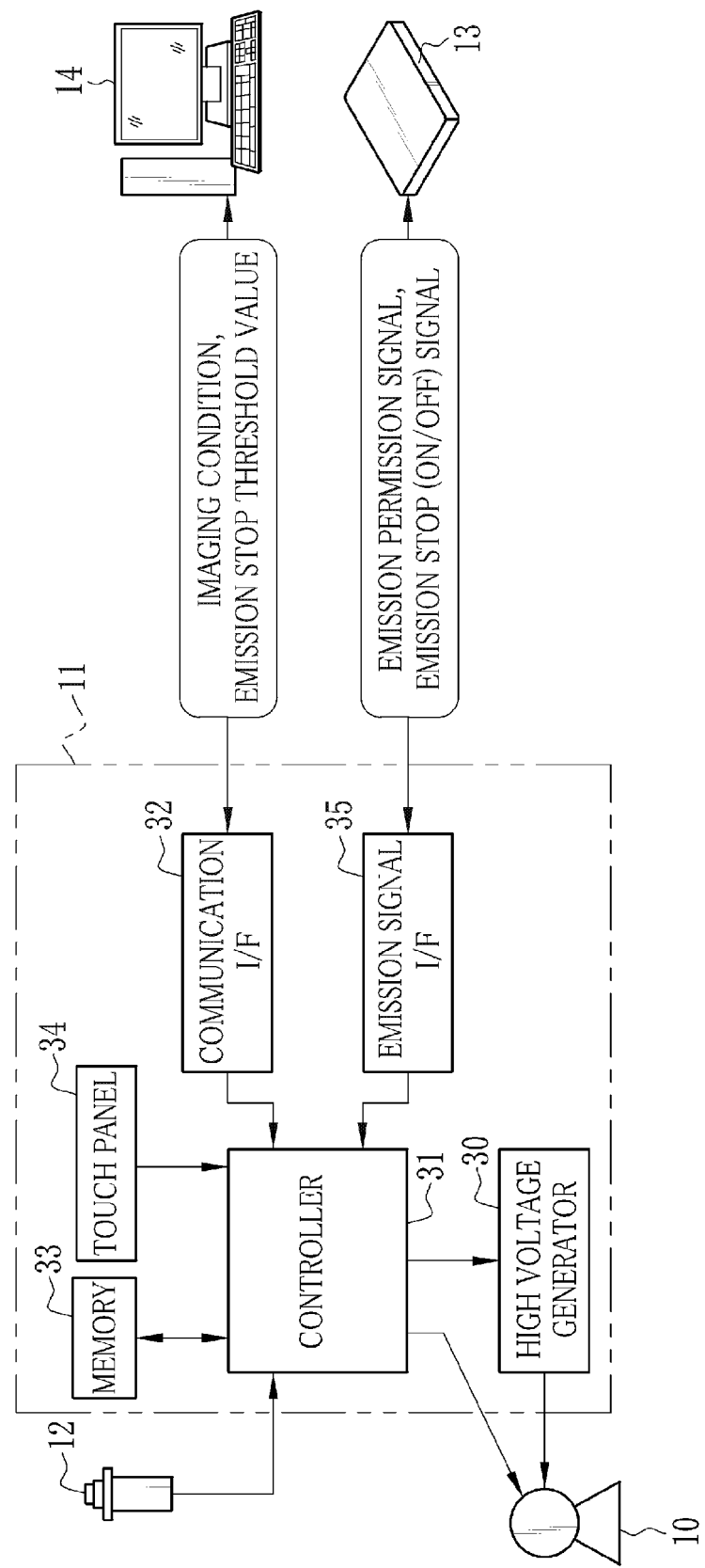
FIG. 2 is a diagram showing the internal structure of an source control device and the relation of connection between the source control device and other devices.

In FIG. 2, the source control device 11 is provided with a high voltage generator 30 that generates a high tube voltage by multiplying an input voltage using a transformer and supplies the X-ray source 10 with the high tube voltage through a high voltage cable, a controller 31 that controls the tube voltage for determining a energy spectrum of the X-rays emitted from the X-ray source 10, a tube current for determining an emission amount per unit of time, and an emission time of the X-rays, and a communication I/F 32 that mediates transmission and reception of fundamental information and signals to and from the console 14.

The emission switch 12, a memory 33, and a tough panel 34 are connected to the controller 31. The emission switch 12 is a two-step press switch to be operated by an operator. Upon a first-step press of the emission switch 12, a warm-up start signal is issued to start warming up the X-ray source 10. Upon a second-step press, an emission start signal is issued to make the X-ray source 10 start emitting the X-rays. These signals are inputted to the source control device 11 through a signal cable. Upon receiving the emission start signal from the emission switch 12, the high voltage generator 30 starts supplying electric power to the X-ray source 10.

The memory 33 stores in advance a plurality of types of imaging conditions, each including the tube voltage, the tube current, and a tube current-emission time product (mAs value) being a product of the tube current and the emission time. The imaging condition is set manually by the operator through the touch panel 34.

A radiation dose required for obtaining an X-ray image of favorable image quality is determined approximately in accordance with a body part to be imaged. However, X-ray transmittance varies according to physique of the object, so even if the same amount of the X-rays is applied, the radiation dose received by the FPD 45 of the electronic cassette 13 varies depending on the physique of the object. For this reason, the X-ray imaging system 2 carries out AEC such that the electronic cassette 13 can obtain the adequate radiation dose irrespective of variations in the physique of the object.

The source control device 11 starts emitting the X-rays with the tube voltage and the tube current-emission time product of the set imaging condition. The AEC has the function of stopping the X-ray emission, upon detecting that the received radiation dose has reached an adequate value, even before reaching the tube current-emission time product set in the source control device 11. Note that, the imaging condition set in the X-ray source 10 has a value with a margin with respect to the adequate value of the radiation dose, in order to prevent a shortage of the radiation dose, in other words, prevent a situation where the X-ray emission is completed before the received radiation dose has reached the adequate value and the AEC judges a stop of the emission. Note that, a value of the tube current-emission time product to be set preferably depends on the body part to be imaged. Instead of the tube current-emission time product, the tube current and the emission time may be set independently.

An emission signal I/F 35 is a connection I/F communicatably connected to the electronic cassette 13, to perform synchronization control for synchronizing operation timing of the source control device 11 and the electronic cassette 13. Upon receiving the warm-up start signal from the emission switch 12, the controller 31 transmits an emission start request signal, which inquires whether or not to permit the start of the X-ray emission, to the electronic cassette 13 through the emission signal I/F 35. Then, in response to the emission start request signal, the controller 31 receives an emission permission signal, which represents that the electronic cassette 13 is ready for receiving the X-ray emission, from the electronic cassette 13 through the emission signal I/F 35. Furthermore, the electronic cassette 13 has an AEC function, and outputs an emission stop signal to make the X-ray source 10 stop emitting the X-rays. The controller 31 receives the emission stop signal through the emission signal I/F 35.

When the emission signal I/F 35 receives the emission permission signal and the controller 31 receives the emission start signal from the emission switch 12, the controller 31 starts the electric power supply from the high voltage generator 30 to the X-ray source 10. As soon as the emission signal I/F 35 has received the emission stop signal from the electronic cassette 13, the controller 31 stops the electric power supply from the high voltage generator 30 to the X-ray source 10 and stops the X-ray emission.

The electronic cassette 13 is composed of the FPD 45 and a portable housing (not shown) for containing the FPD 45. The housing of the electronic cassette 13 is in an approximately rectangular and flat shape, and of the same size (a size compatible with International Standard ISO4090:2001) as a film cassette and an IP cassette (also called a CR cassette) in plane. Therefore, the electronic cassette 13 is attachable to an existing imaging stand designed for the film cassette and the IP cassette.

A plurality of electronic cassettes 13 are provided in one examination room installed with the X-ray imaging system 2, for example, two electronic cassettes 13, one for the imaging stand 15 and the other for an imaging table are provided. The electronic cassette 13 is detachably loaded into a holder 18 of the imaging stand 15 in such a position that an imaging surface 47 of the FPD 45 is opposed to the X-ray source 10, more specifically, the center of the imaging surface 47 is disposed in an extension of a normal extending from a focus of the X-ray tube 16 along a Y direction (a direction parallel to the floor of the examination room and orthogonal to the X direction). The electronic cassette 13 can be used separately without being loaded into the imaging stand 15 or the imaging table, in a state of being put on a bed under the object lying or held by the object himself/herself.

The console 14 is communicatably connected to the electronic cassette 13 by a wired or wireless method, and controls the operation of the electronic cassette 13 in response to an input operation of the operator through an input device 19 such as a keyboard. To be more specific, the console 14 controls power-on and -off of the electronic cassette 13, mode switching to a standby mode or an imaging mode, and the like.

The console 14 applies various types of image processes such as offset correction, gain correction, and defect correction to X-ray image data transmitted from the electronic cassette 13. In the defect correction, pixel values of a column having a detection pixel 65 are interpolated with pixel values of an adjacent column having no detection pixel 65. Note that, the electronic cassette 13 may perform the above various types of image processes, instead.

The X-ray image after being subjected to the image processes is displayed on a display 20 of the console 14, and its data is stored to a memory 101 or a storage device 102 of the console 14 or a data storage such as an image storage server connected to the console 14 through a network.

The console 14 receives input of an examination order including information about sex and age of a patient, a body part to be imaged, and an examination purpose, and displays the examination order on the display 20. The examination order is inputted from an external system e.g. a HIS (hospital information system) or a RIS (radiography information system) that manages patient data and examination data related to radiography, or inputted manually by the operator. The examination order includes the body part to be imaged e.g. a head, a chest, an abdomen, and the like, and an imaging direction e.g. anterior, medial, diagonal, PA (the X-rays are applied from a posterior direction), and AP (the X-rays are applied from an anterior direction). The operator confirms the contents of the examination order on the display 20, and inputs the imaging condition corresponding to the contents to an operation screen displayed on the display 20. With referring to the imaging condition inputted to the console 14, the same imaging condition is inputted to the source control device 11.

Figure 3:
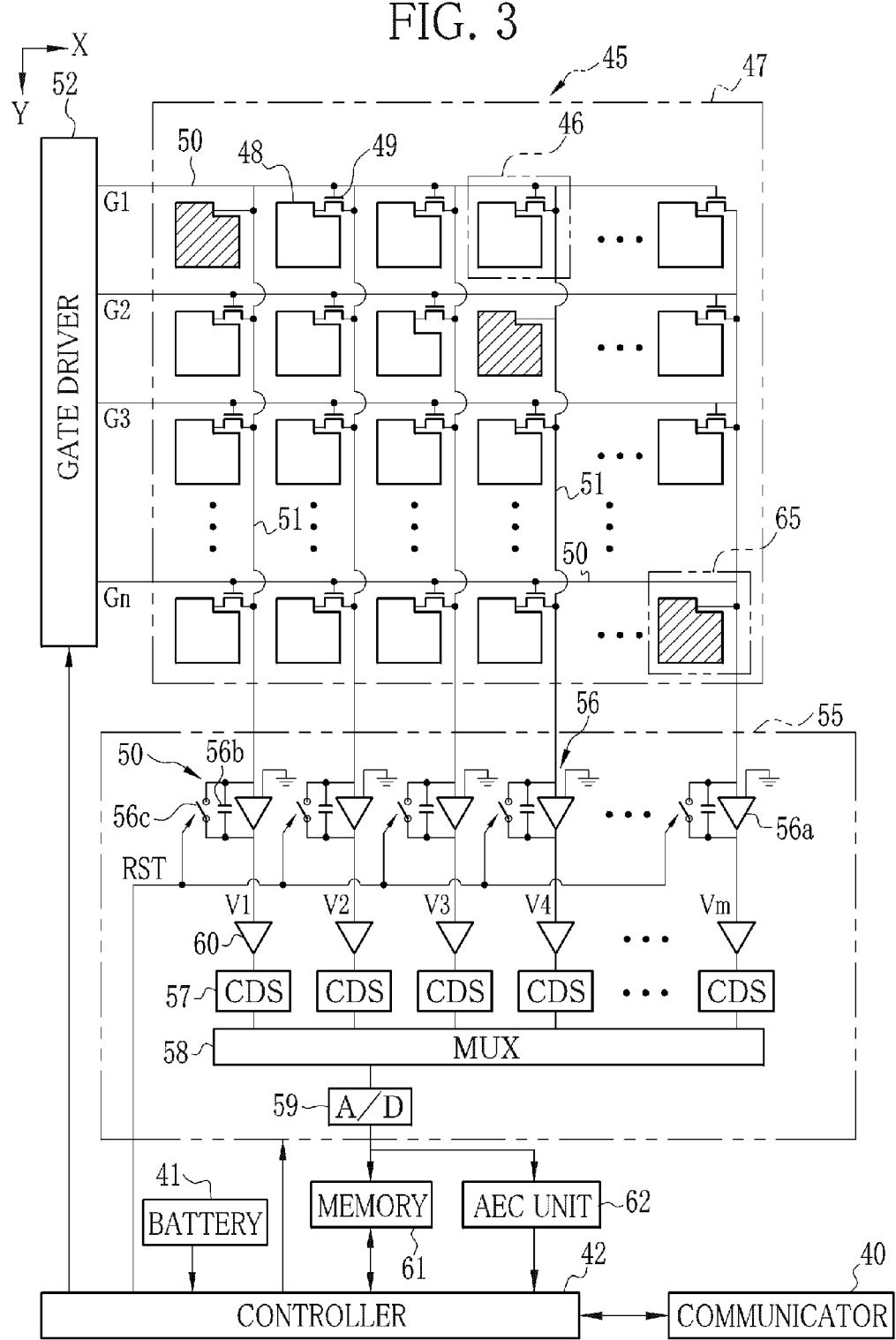
FIG. 3 is a block diagram showing the internal structure of an electronic cassette.

In FIG. 3, the electronic cassette 13 contains a communicator 40 for communicating with the console 14 by the wired or wireless method, and a battery 41. The communicator 40 mediates transmission and reception of various types of information and signals including image data between the console 14 and a controller 42. The battery 41 supplies electric power to operate each part of the electronic cassette 13. The battery 41 is of a relatively small type so as to be contained in the slim electronic cassette 13. The battery 41 can be taken out of the electronic cassette 13 and set in a specific cradle for recharging. The battery 41 may be wirelessly rechargeable.

The communicator 40 is connected to the console 14 with a cable, in a case where the wireless communication between the electronic cassette 13 and the console 14 is disabled due to weak incoming signal strength or the like. Connecting the cable from the console 14 to the communicator 40 establishes wired communication with the console 14. A multi-cable into which a communication cable and a power supply cable are integrated may be used to supply power to the electronic cassette 13 and recharge the battery 41 from the console 14 or utility power.

The FPD 45, being a detection panel for detecting the X-ray image, has a TFT active matrix substrate. In this substrate, a plurality of pixels 46 each for accumulating electric charge in accordance with a received X-ray dose are arranged to form the imaging surface 47. The plurality of pixels 46 are arranged into a two-dimensional matrix with n rows (X direction) and m columns (Y direction) at a predetermined pitch. "n" and "m" are integers of 2 or more. The pixel number of the FPD 45 is, for example, approximately 2000 by approximately 2000.

The FPD 45 is of an indirect conversion type, having a scintillator (phosphor) for converting the X-rays into visible light. The pixels 46 perform photoelectric conversion of the visible light converted by the scintillator. The scintillator is made of CsI:Tl (thallium activated cesium iodide), GOS ($Gd_2O_2S$:Tb, gadolinium oxysulfide), or the like, and is opposed to the entire imaging surface 47 having the matrix of pixels 46. Note that, the scintillator and the TFT active matrix substrate may be disposed in either a PSS (penetration side sampling) method in which the scintillator and the substrate are disposed in this order from an X-ray incident side, or an ISS (irradiation side sampling) method in which the substrate and the scintillator are disposed in this order, oppositely to the PSS method. Another FPD of a direct conversion type, which has a conversion layer (amorphous selenium or the like) for directly converting the X-rays into the electric charge without using the scintillator, may be used instead.

The pixel 46 is composed of a photodiode 48 being a photoelectric conversion element for producing the electric charge (electron and hole pairs) upon incidence of the visible light, a capacitor (not shown) for accumulating the electric charge produced by the photodiode 48, and a thin film transistor (TFT) 49 being a switching element.

The photodiode 48 is composed of a semiconducting layer (of a PIN type, for example) for producing the electric charge and an upper electrode and a lower electrode disposed on the top and bottom of the semiconducting layer. The lower electrode of the photodiode 48 is connected to the TFT 49. The upper electrode of the photodiode 48 is connected to a bias line. There are the same number of the bias lines provided as the number of the rows (n rows) of the pixels 46 in the imaging surface 47. All the bias lines are coupled to a bus. The bus is connected to a bias power supply. A bias voltage is applied from the bias power supply to the upper electrodes of the photodiodes 48 through the bus and the bias lines. Since the application of the bias voltage produces an electric field in the semiconducting layer, the electric charge (electron and hole pairs) produced in the semiconducting layer by the photoelectric conversion is attracted to the upper and lower electrodes, one of which has a positive polarity and the other of which has a negative polarity. Thereby, the electric charge is accumulated in the capacitor.

A gate electrode of the TFT 49 is connected to a scan line 50. A source electrode of the TFT 49 is connected to a signal line 51. A drain electrode of the TFT 49 is connected to the photodiode 48. The scan lines 50 and the signal lines 51 are routed into a lattice. The number of the scan lines 50 coincides with the number of the rows (n rows) of the pixels 46 in the imaging surface 47. The number of the signal lines 51 coincides with the number of the columns (m columns) of the pixels 46. The scan lines 50 are connected to a gate driver 52, and the signal lines 51 are connected to a signal processing circuit 55.

The gate driver 52 drives the TFTs 49 to carry out an accumulation operation for accumulating signal charge in the pixels 46 in accordance with the received X-ray dose, a readout operation (actual readout operation) for reading out the signal charge from the pixels 46, and a reset operation (idle readout operation). The controller 42 controls start timing of each of the above operations carried out by the gate driver 52.

In the accumulation operation, the signal charge is accumulated in the pixels 46 while the TFTs 49 are turned off. In the readout operation, the gate driver 52 sequentially issues gate pulses G1 to Gn each of which drives the TFTs 49 of the same row at a time. Thereby, the scan lines 50 are activated one by one, and the TFTs 49 connected to the activated scan line 50 are turned on, on a row-by-row basis. Upon turning on the TFT 49, the electric charge accumulated in the capacitor of the pixel 46 is read out to the signal line 51 and inputted to the signal processing circuit 55.

The signal processing circuit 55 includes integration amplifiers 56, CDS circuits (CDSs) 57, a multiplexer (MUX) 58, an A/D converter (A/D) 59, and the like. The integration amplifier 56 is connected to each signal line 51 on a one-by-one basis. The integration amplifier 56 is composed of an operational amplifier 56*a* and a capacitor 56*b* connected between input and output terminals of the operational amplifier 56*a*. The signal line 51 is connected to one of the input terminals of the operational amplifier 56*a*. The other input terminal of the operational amplifier 56*a* is connected to a ground (GND). A reset switch 56*c* is connected in parallel with the capacitor 56*b*. The integration amplifier 56 converts by integration the electric charge inputted from the signal line 51 into each of analog voltage signals V1 to Vm, and outputs each of the voltage signals V1 to Vm. An output terminal of the operational amplifier 56a of each column is connected to the MUX 58 through another amplifier 60 and the CDS 57. An output of the MUX 58 is connected to the A/D 59.

The CDS 57 has sample hold circuits. The CDS 57 removes noise from an output voltage signal of the integration amplifier 56 by correlated double sampling, and holds (sample hold) the output voltage signal of the integration amplifier 56 at its sample hold circuit for a predetermined period. The MUX 58 sequentially selects one of the CDSs 57 connected in parallel based on an operation control signal from a shift resistor (not shown), and inputs the voltage signals V1 to Vm outputted from the CDSs 57 in series to the A/D converter 59. Note that, another amplifier may be connected between the MUX 58 and the A/D converter 59.

The A/D converter 59 converts the inputted analog voltage signals V1 to Vm of one row into digital values, and outputs the digital values to a memory 61 of the electronic cassette 13. To the memory 61, the digital values of one row are recorded with being associated with coordinates (addresses having a row number and a column number) of the individual pixels 46 in the imaging surface 47, as image data representing the X-ray image of one row. Thereby, the readout operation of one row is completed.

After the MUX 58 reads out the voltage signals V1 to Vm of one row from the integration amplifiers 56, the controller 42 outputs a reset pulse RST to the integration amplifiers 56 to turn on the reset switches 56c. Thus, the signal charge of one row accumulated in the capacitors 56b is reset. After the reset of the integration amplifiers 56, the reset switches 56c are turned off again. After a lapse of predetermined time, one of the sample hold circuits of the CDS 57 holds to sample a kTC noise component of the integration amplifier 56. After that, the gate driver 52 outputs the gate pulse of the next row to start reading out the signal charge from the pixels 46 of the next row. By sequential repetition of this operation, the signal charge is read out from the pixels 46 of every row.

After the completion of the readout from every row, image data representing the X-ray image of one frame is recorded to the memory 61. This image data is read out from the memory 61, and outputted to the console 14 through the communicator 40. Thereby, the X-ray image of the object is detected.

Dark charge occurs in the semiconducting layer of the photodiode 48 irrespective of the presence or absence of the incidence of the X-rays. Due to the application of the bias voltage, the dark charge is accumulated in the capacitor of the pixel 46. The dark charge occurring in the pixels 46 becomes a noise component of the image data, and therefore the reset operation is carried out to remove the dark charge. The reset operation is an operation to discharge the dark charge occurring in the pixels 46 through the signal lines 51.

The reset operation adopts a sequential reset method, for example, by which the pixels 46 are reset on a row-by-row basis. In the sequential reset method, as with the readout operation of the signal charge, the gate driver 52 sequentially issues the gate pulses G1 to Gn to the scan lines 50 to turn on the TFTs 49 of the pixels 46 on a row-by-row basis. While the TFT 49 is turned on, the dark charge flows from the pixel 46 through the signal line 51 into the capacitor 56b of the integration amplifier 56. In the reset operation, in contrast to the readout operation, the MUX 61 does not read out the electric charge accumulated in the capacitor 56b. In synchronization with the issue of each of the gate pulses G1 to Gn, the controller 42 outputs the reset pulses RST to turn on the reset switches 56c. Thereby, the electric charge accumulated in the capacitors 56b is discharge, and the integration amplifiers 56 are reset.

Instead of the sequential reset method, a parallel reset method in which a plurality of rows of pixels are grouped together, and sequential reset is carried out in each group so as to concurrently discharge the dark charge from the rows of the number of the groups, or all pixels reset method in which the gate pulse is inputted to every row to discharge the dark charge from every pixel at a time may be used. The parallel reset method and the all pixels reset method allow speeding up the reset operation.

The FPD 45 has, in the same imaging surface 47, a plurality of detection pixels 65 each of which is connected to the signal line 51 without interposition of the TFT 49, in addition to the normal pixels 46 each connected to the signal line 51 through the TFT 49 as described above. The detection pixels 65 are pixels for use in detecting the X-ray dose received by the imaging surface 47, and function as AEC sensors (dose detection sensors). The detection pixel 65 is used for outputting the emission stop signal as soon as an integrated value of the received X-ray dose has reached a predetermined value. The detection pixels 65 occupy on the order of several ppm (parts per million) to several % of the pixels 46 in the imaging surface 47.

Figure 4:
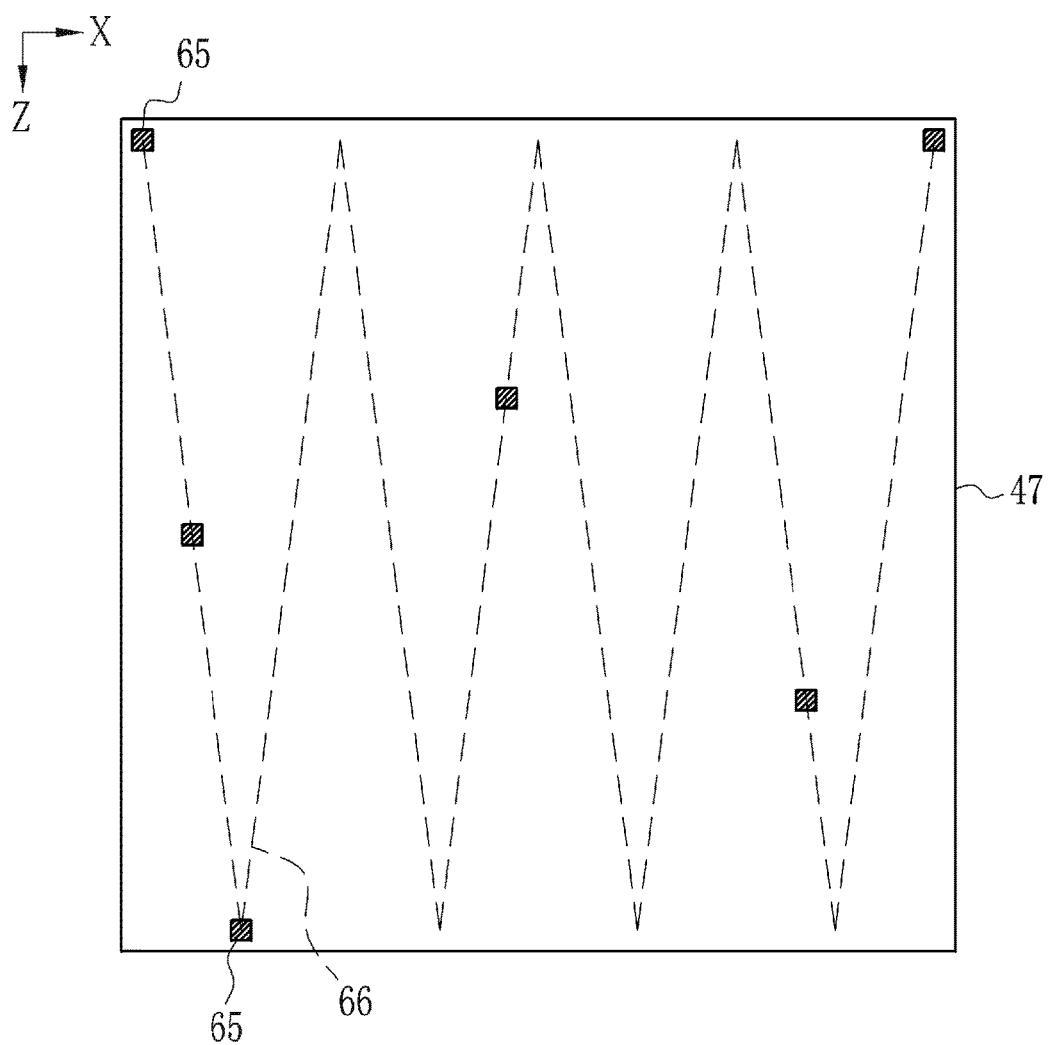
FIG. 4 is a diagram of explaining the disposition of detection pixels.

As shown in FIG. 4, the detection pixels 65 are disposed along a waveform line 66 that is horizontally symmetric with respect to the center of the imaging surface 47 as shown by a broken line, so as to be uniformly distributed in the imaging surface 47 without being localized. One detection pixel 65 is laid out in the column of the pixels 46 connected to the single signal line 51. The columns having the detection pixel 65 are arranged at intervals of two to three columns having no detection pixel 65. The position of the detection pixels 65 is known in manufacturing the FPD 45, and the FPD 45 has a nonvolatile memory (not shown) that stores in advance the position (coordinates) of every detection pixel 65 in the imaging surface 47. Note that, oppositely to this embodiment, the detection pixels 65 may be disposed in a localized manner. The disposition of the detection pixels 65 is arbitrarily changeable. For example, in the case of a mammography device for imaging a breast, it is preferable to dispose the detection pixels 65 on a thoracic wall side in a localized manner.

Since the detection pixel 65 is connected to the signal line 51 directly without interposition of the TFT 49, the signal charge produced in the detection pixel 65 immediately flows into the signal line 51. The same holds true, even while the TFTs 49 of the normal pixels 46 of the same column are turned off and the normal pixels 46 of the same column are in the accumulation operation. Thus, the electric charge produced in the detection pixel 65 always flows into the capacitor 56b of the integration amplifier 56 in the signal line 51 connected to the detection pixel 65. During the accumulation operation, the electric charge that is produced in the detection pixel 65 and accumulated in the integration amplifier 56 is outputted to the A/D converter 59 at a predetermined sampling period. The A/D converter 59 converts the analog voltage signal into the digital value (hereinafter called a dose detection signal). The dose detection signal is outputted to the memory 61. The memory 61 stores the dose detection signal with being associated with the coordinates in the imaging surface 49. The FPD 45 repeats this dose detection operation over a plurality of times at a predetermined sampling rate.

The controller 42 controls the operation of an AEC unit 62. The AEC unit 62 reads out the dose detection signals that are obtained over the plurality of times at the predetermined sampling rate from the memory 61, and performs the AEC based on the read dose detection signals. The dose detection signal obtained by one-time sampling is an instantaneous value of the X-ray dose received by the imaging surface 47. The AEC unit 62 calculates an integrated value of the X-ray dose received by the imaging surface 47 by sequentially adding the dose detection signals obtained by several-time sampling on a coordinate-by-coordinate basis.

Figures 5, 6:
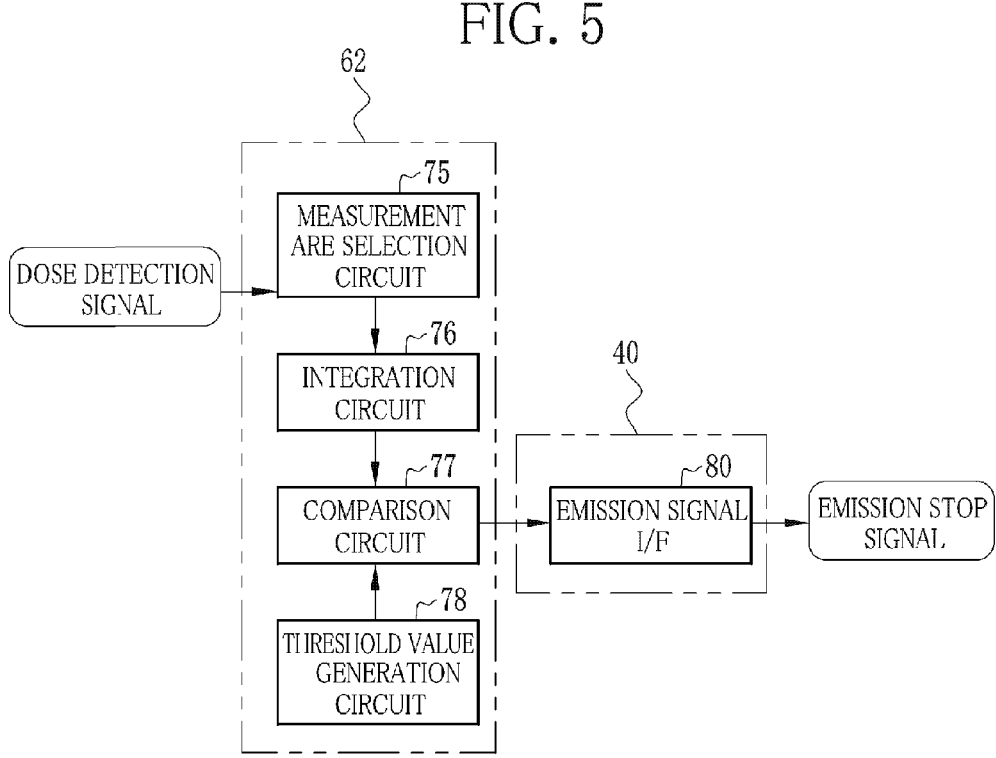
FIG. 5 is a block diagram showing the internal structure of an AEC unit and a communicator of the electronic cassette.
FIG. 6 is a table of imaging conditions set in a console.

In FIG. 5, the AEC unit 62 has a measurement area selection circuit 75, an integration circuit 76, a comparison circuit 77, and a threshold value generation circuit 78. The measurement area selection circuit 75 selects a measurement area corresponding to a region of interest that is the most noteworthy in making a diagnosis, out of the imaging surface 47. Specifically speaking, the selection of the measurement area is performed by selecting the detection pixel 65 situated in the selected measurement area.

Taking the case of chest radiography for diagnosing a lung condition as an example, the region of interest is right and left lung fields. In the chest radiography, a chest of the object is necessarily opposed to the imaging surface 47, and apart of arms and an abdomen, in addition to the chest, is opposed to the imaging surface 47 too. The imaging surface 47 includes not only an object area opposed to the object, but also a directly exposed area on which the X-rays are directly incident without passing through the object. The measurement area selection circuit performs a two-step area determination process, i.e. firstly determines the object area excluding the directly exposed area in the imaging surface 47, and then determines the measurement area being the region of interest out of the determined object area.

Since the directly exposed area is an area on which the X-rays are directly incident without passing through the object, an expected value of the received dose (first expected received dose) of the directly exposed area can be obtained by calculation using the imaging condition (the tube voltage and the tube current) and the like, independently of which body part of the object is imaged. The measurement area selection circuit 75 determines the directly exposed area based on comparison between the dose detection signals outputted from the detection pixels 65 in the imaging surface 47 with the first expected received dose. An area excluding the determined directly exposed area is determined as the object area.

In the chest radiography, the measurement area selection circuit 75 determines the right and left lung fields corresponding to the region of interest as the measurement area, out of the determined object area. In the imaging field 47, the position and the size of areas opposed to the right and left lung fields can be known roughly, but the position and the size of the lung fields are different depending on the physique of the patient. For example, the position and the size of a human body are different between an adult and a child or between a male and a female, so the position and the size of the lung fields differ too. Among adult males, the position and the size of the lung fields are different in accordance with a height and a width of his body. Thus, if the measurement areas are determined with respect to the position and the size of the lung fields of an adult male, for example, in a case where the patient is a child having smaller lung fields than the adult male has, an area other than the lung field is included in the measurement area. This hinders measurement of the appropriate X-ray dose applied to the lung fields.

Therefore, an expected received dose (a second expected received dose) of the measurement area, being the region of interest, is obtained in advance by simulation. The measurement area selection circuit 75 chooses the measurement area, being the region of interest, in the imaging surface 47 based on the second expected received dose. The second expected received dose is a radiation dose that is expected to be received by the region of interest. In a case where the region of interest is the lung fields, for example, the second expected received dose is a radiation dose that is expected to be received by the lung fields. A thorax has a mediastinum between the right and left lung fields, a heart under the mediastinum, and a diaphragm under the lung fields. X-ray absorptance is different between the lung fields and the other part around the lung fields, so the received dose differs between the lung fields and the other part even if the same radiation dose is applied. The measurement area selection circuit 75 determines the areas corresponding to the lung fields in the imaging surface 47 by comparison between the second expected received dose of the lung fields and the dose detection signals of the detection pixels 65, and determines the area as the measurement area.

The second expected received dose is calculated in advance by experiment and simulation based on a physique of a normal-size adult male, for example. A body thickness exerts an influence upon the X-ray absorptance of the lung fields, as a matter of course. Therefore, in a case where the dose detection signal of the detection pixel 65 is within the predetermined confines centering on the second expected received dose, if not coincides with the second expected received dose, the measurement area selection circuit 75 judges an area having the detection pixel 65 as the lung field. This facilitates determining the lung fields, even if the body thickness is thicker or thinner than normal, or the patient is not an adult male but an adult female, a child, or the like.

The second expected received dose is a value to be compared with the dose detection signals detected by the detection pixels 65, in a duration of time that the measurement area selection circuit 75 carries out a measurement area selection process. Thus, the second expected received dose is a value that is expected to be received in an emission time set within the duration. For example, if the duration of time for carrying out the measurement area selection process is 10 msec, an emission time of 10 msec or less is set in the simulation, and a value of the radiation dose expected to be received within the emission time is recorded. To be more specific, a value that is comparable with the dose detection signals obtained by the several-time to several-tens-time sampling is calculated by the simulation.

The integration circuit 76 integrates a typical value of the measurement area, such as an average value, a maximum value, a mode value, or a sum value of the dose detection signals from the detection pixels 65 chosen by the measurement area selection circuit 75. Upon starting the X-ray emission, the comparison circuit 77 starts monitoring an integrated value of the dose detection signals from the integration circuit 76. The comparison circuit 77 compares the integrated value with an emission stop threshold value provided by the threshold value generation circuit 78 at appropriate timing. As soon as the integrated value has reached the threshold value, the comparison circuit 77 outputs the emission stop signal.

The communicator 40 has an emission signal I/F 80. The emission signal I/F 35 of the source control device 11 is connected to the emission signal I/F 80. The emission signal I/F 80 performs reception of the emission start request signal, transmission of the emission permission signal in response to the emission start request signal, and output of the comparison circuit 77 i.e. transmission of the emission stop signal.

As shown in FIG. 6, the console 14 is set with the imaging condition including the tube current and the tube voltage corresponding to the body part to be imaged (the chest or the head), the second expected received dose and the emission stop threshold value corresponding to the imaging condition, and the like. As described above, the second expected received dose is information to be referred by the measurement area selection circuit 75 performing the measurement area selection process. The emission stop threshold value is read out by the threshold value generation circuit 78. The emission stop threshold value is information to be compared with the integrated value of the dose detection signal of the detection pixel 65 in the measurement area, so that the AEC unit 62 judges the stop of the X-ray emission. These information is stored in the storage device 102.

Note that, FIG. 6 shows only the chest and the head as examples of the body part to be imaged in FIG. 6, but in actual fact, the imaging conditions of other body parts, such as an abdomen, a leg, a full spine covering an upper body extending from a thorax to a waist in continuous imaging, and a lower limb covering a lower body extending from a waist to toes in continuous imaging, and the second expected received doses and the emission stop threshold values of the body parts are recorded too. As for the second expected received dose, one typical value is set as an example, but a plurality of types of values may be stored in accordance with the physique (the body thickness) of the object M, such as thin, normal, and fat. The physique (the body thickness) of the object M is inputted, and the second expected threshold value may be varied in accordance with the inputted physique (the body thickness). One type of region of interest is set with respect to each body part, such that the lung fields are the region of interest in the chest, but a plurality of types of regions of interest may be set in each body part. In this case, the second expected received dose and the emission stop threshold value vary from region to region.

Figure 7:
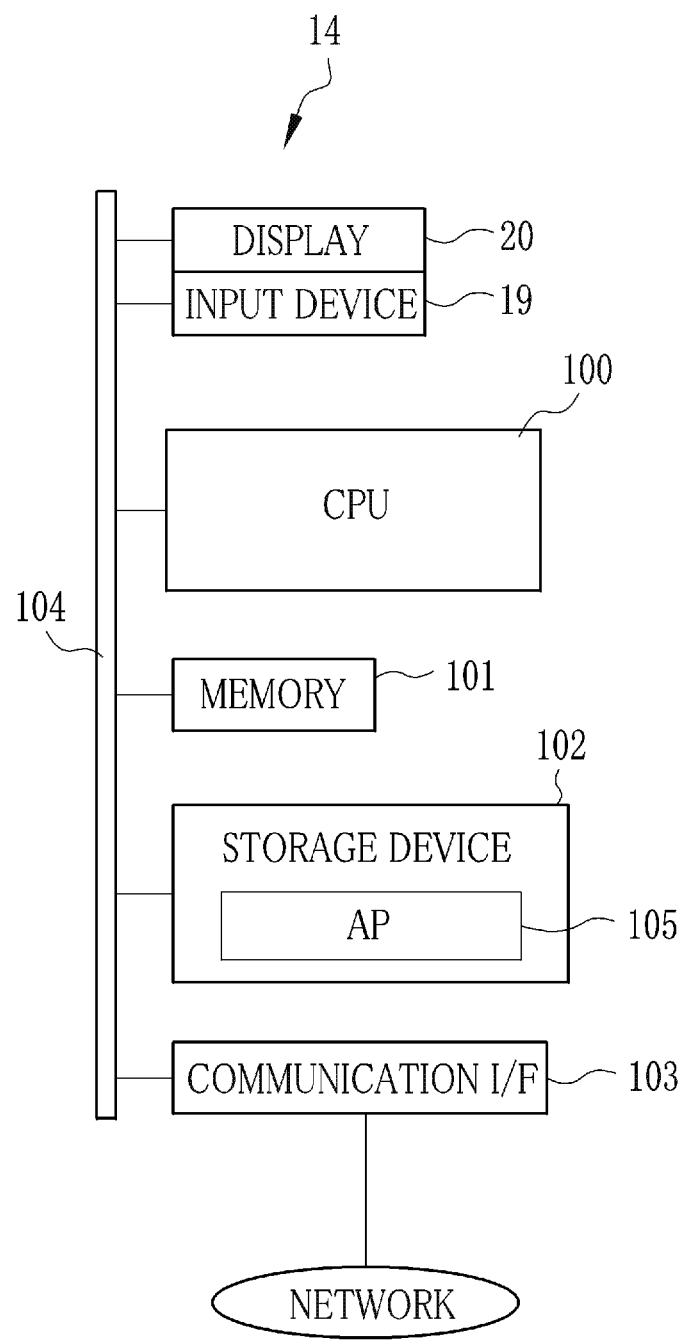
FIG. 7 is a block diagram showing the internal structure of the console.

In FIG. 7, the console 14 is composed of a computer having a CPU 100, the memory 101, the storage device 102, and a communication I/F 103, in addition to the input device 19 and the display 20 described above. These components are connected to each other via a data bus 104.

The storage device 102 is a HDD (hard disk device), for example. The storage device 102 stores a control program and an application program (hereinafter called an AP) 105. The AP 105 is a program that makes the console 14 perform various functions related to the X-ray imaging, including a display process of the examination order and the X-ray image, the image process to be applied to the X-ray image, setting of the imaging condition, and the like.

Figure 14:
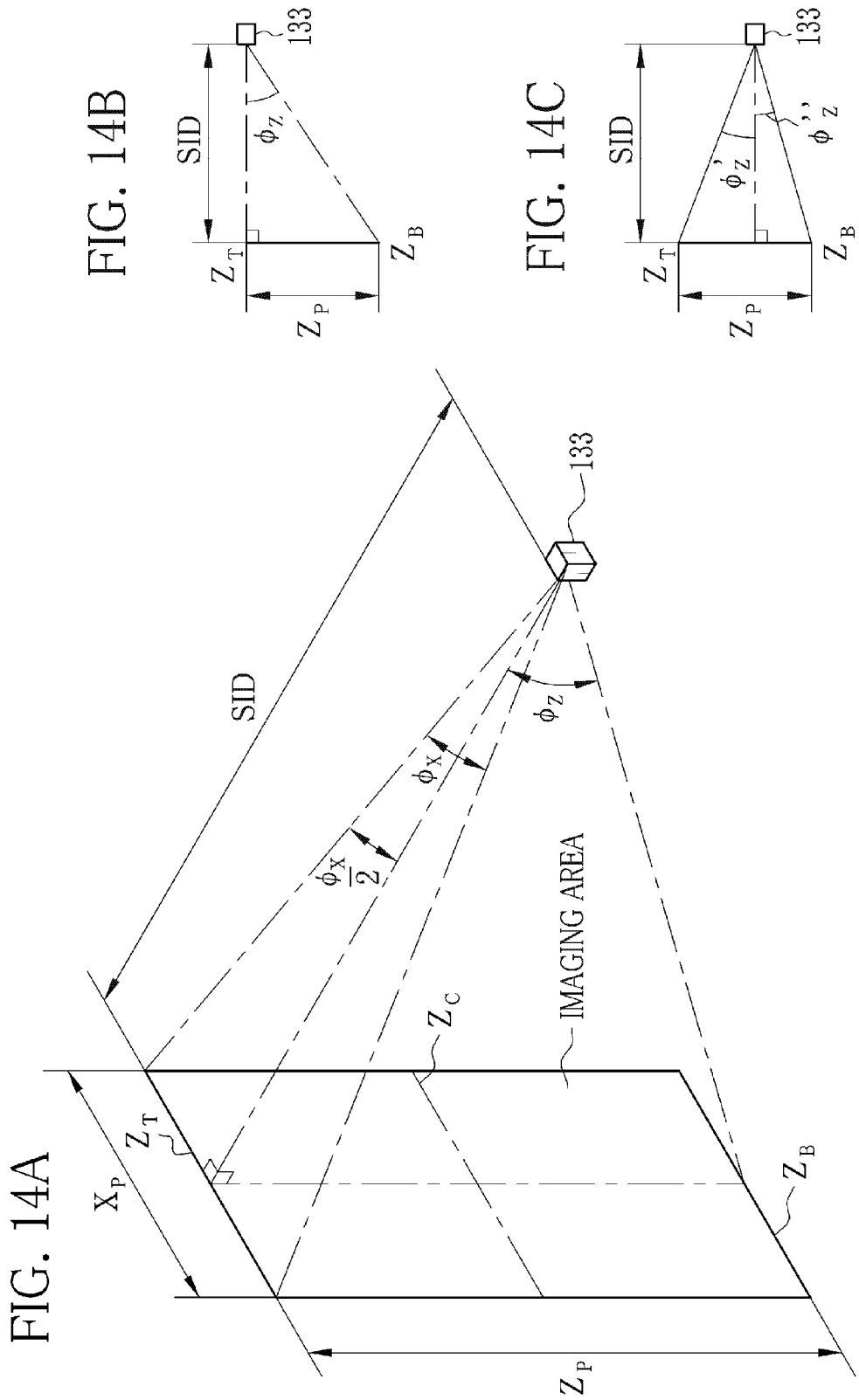
FIGS. 14A to 14C are diagrams showing a state of setting an imaging area in the continuous imaging.

The memory 101 is a work memory used in executing processes by the CPU 100. The CPU 100 loads the control program stored in the storage device 102 into the memory 101, and runs the program to make centralized control of each part of the computer. The communication I/F 103 is a network interface for performing wireless or wired transmission control with an external device such as the RIS, the HIS, the image storage server, and the electronic cassette 13. The input device 19 includes a keyboard and a mouse, a touch panel integrated with the display 20, or the like. The input device 19 is operated in setting the imaging condition, in inputting a distance SID (source image distance, see FIG. 1) from the position $Y_0$ of the imaging surface 47 of the FPD 45 to the position $Y_1$ of the focus of the X-ray tube 16, and widths $X_P$ and $Z_P$ (see FIG. 14) of an imaging area in X and Z directions (see FIG. 1) being an area to which X-rays are applied in the imaging surface 47, and the like.

Figure 8:
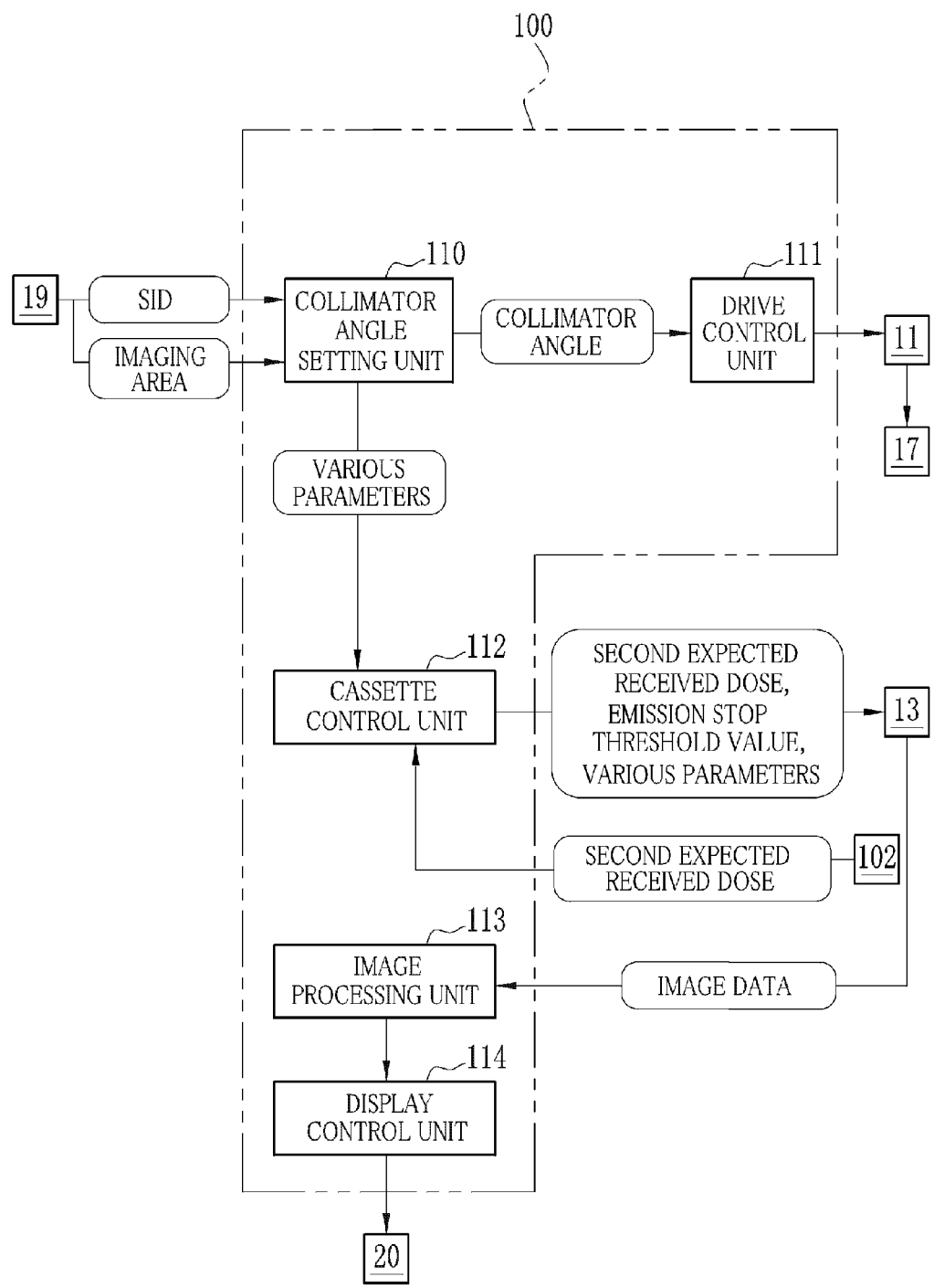
FIG. 8 is a block diagram showing the function of the console and an information flow.

In FIG. 8, running the AP 105 makes the CPU 100 of the console 14 function as a collimator angle setting unit 110, a drive control unit 111, a cassette control unit 112, an image processing unit 113, and a display control unit 114. The collimator angle setting unit 110 sets a collimator angle of the irradiation field limiter 17. The drive control unit 111 drives the irradiation field limiter 17 through the source control device 11 in accordance with a condition set in the collimator angle setting unit 110. The image processing unit 113 applies various types of image processes including the offset correction, the gain correction, the defect correction, and the like as described above, to produce the image data. The display control unit 114 displays the X-ray image based on the image data, an operation menu required in making an exposure, and the like on the display 20.

The collimator angle setting unit 110 calculates the collimator angle based on the SID and the widths $X_P$ and $Z_P$ of the imaging area in the X and Z directions inputted from the input device 19. A collimator angle $\theta_X$ in the X direction is calculated by the following expression (1-1). A collimator angle $\theta_Z$ in the Z direction can be calculated by the following expression (1-2):

$$\theta_X = 2 \times \tan^{-1}\{(X_P/2)/\text{SID}\} \qquad \text{Expression (1-1)}$$

$$\theta_Z = 2 \times \tan^{-1}\{(Z_P/2)/\text{SID}\} \qquad \text{Expression (1-2)}$$

The source control device 11 drives the irradiation field limiter 17 using the collimator angles $\theta_X$ and $\theta_Z$ calculated by the collimator angle setting unit 110. Note that, the widths $X_P$ and $Z_P$ of the imaging area are set at the widths of the imaging surface 47 in the X and Z directions by default. The widths $X_P$ and $Z_P$ of the imaging area are appropriately changed by the operator, in a case where the size of the body part to be imaged is smaller than the imaging surface 47, e.g. the lateral width of the body is narrow because the object M is thin.

The cassette control unit 112 reads out from the storage device 102 information about the second expected received dose and the emission stop threshold value (E1, E2, TH1, and TH2 of FIG. 6) corresponding to the set body part, and provides the electronic cassette 13 with the information. The measurement area selection circuit 75 determines the detection pixels 65 situated in the measurement area corresponding to the region of interest, based on the second expected received dose provided by the cassette control unit 112. The threshold value generation circuit 78 sets the information on the emission stop threshold value provided by the cassette control unit 112, as information to be compared with the integrated value of the dose detection signal in this imaging operation.

Figure 9:
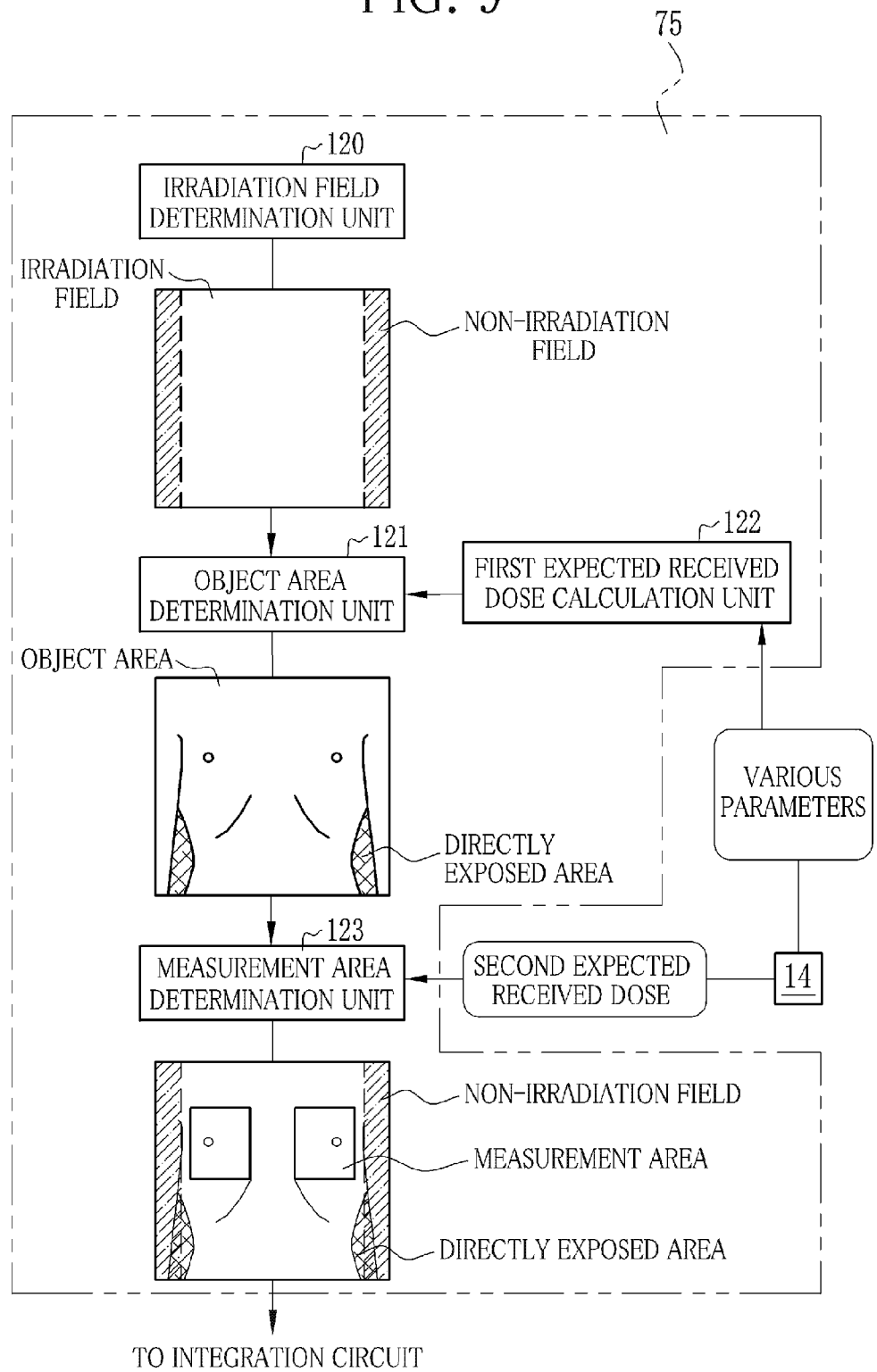
FIG. 9 is a block diagram showing the internal structure of a measurement area selection circuit.

In FIG. 9, the measurement area selection circuit 75 is provided with an irradiation field determination unit 120, an object area determination unit 121, a first expected received dose calculation unit 122, and a measurement area determination unit 123. The irradiation field determination unit 120 determines the irradiation field corresponding to the imaging area in the imaging surface 47 based on the set widths $X_P$ and $Z_P$ of the imaging area. Then, the irradiation field determination unit 120 reads out the dose detection signals, which are outputted from the detection pixels 65 and recorded to the memory 61 on a coordinate-by-coordinate basis of the detection pixels 65, and picks up the dose detection signals that are outputted from the detection pixels 65 situated in the irradiation field, out of all the dose detection signals. In other words, the irradiation field determination unit 120 excludes the dose detection signals of the detection pixels 65 situated in a non-irradiation field (an area to which no X-ray is applied), from candidates for the measurement area. Note that, provided that the widths of the imaging area are set to the default of $X_P$ and $Z_P$, the entire imaging surface 47 is set as the irradiation field. In this situation, the irradiation field determination unit 120 does not operate.

Note that, the irradiation field may be determined by comparing the dose detection signals with a threshold value, which is set therefor. In this case, the dose detection signals of the non-irradiation field to which no X-ray is applied are almost zero, so the threshold value is set at a value near zero (refer to TH0 of FIG. 10). An area that outputs the dose detection signals of the threshold value or less is determined as the non-irradiation field, while the other area is determined as the irradiation field.

The object area determination unit 121 picks up the dose detection signals of the detection pixels 65 situated in the object area to which the X-rays are applied through the object M, out of all the dose detection signals outputted from the detection pixels 65 situated in the irradiation field. In other words, the object area determination unit 121 excludes the dose detection signals of the detection pixels 65 situated in the directly exposed area to which the X-rays are directly applied without passing through the object M, from the candidates for the measurement area.

The first expected received dose calculation unit 122 calculates an expected value (first expected received dose) of the X-ray dose to be received by the directly exposed area in that situation, from a relational expression of a radiation dose and parameters, including the SID, the imaging condition (the tube voltage and the tube current), and the like. Just as with the second expected received dose, the first expected received dose is a value to be compared with the dose detection signals detected by the detection pixels 65, in a duration of time that the measurement area selection circuit 75 carries out the measurement area selection process. Thus, the first expected received dose is a value that is expected to be received within the duration. For example, a value that is comparable with the dose detection signals obtained by the several-time to several-tens-time sampling is calculated. The calculated first expected received dose is outputted to the object area determination unit 121. Various parameters required for determining the irradiation field and calculating the first expected received dose are obtained through the cassette control unit 112.

To calculate the first expected received dose, for example, an area dose expression by a NDD method (a numerical dose determination method) is used. An area dose D is calculated from $$D = T \times C\_kV \times C\_Fil \times mAs \times (1/SID)^2 \times BSF \times AREA \qquad \text{Expression (2)}$$

wherein, T represents a constant determined in accordance with a rectification method (inverter, single-phase, or three-phase) of the high voltage generator 30, C_kV represents a tube voltage correction coefficient, C_Fil represents a tube voltage correction coefficient related to the thickness of various filters provided in the X-ray source 10, mAs represents the tube current-emission time product, BSF represents a back scattering correction coefficient, and AREA represents the irradiation field of the X-rays in the imaging surface 47. The above T, C_kV, and the like are stored in the storage device 102 in a data table format. The cassette control unit 112 reads out values corresponding to specifications of the X-ray source 10 and the high voltage generator 30 from the storage device 102, and provides the values to the first expected received dose calculation unit 122.

The object area determination unit 121 compares the first expected received dose from the first expected received dose calculation unit 122 with the dose detection signals of the detection pixels 65 situated in the irradiation field. The detection pixels 65 that output the dose detection signals of the first expected received dose or more are determined to be situated in the directly exposed area, and the other detection pixels 65 are determined to be situated in the object area. Otherwise, the detection pixels 65 whose dose detection signals are within the predetermined confines (first expected received dose±α) centering on the first expected received dose may be determined to be situated in the directly exposed area. Thereby, the irradiation field determination unit 120 and the object area determination unit 121 exclude the dose detection signals of the detection pixels 65 situated in the non-irradiation field and the directly exposed area, from the candidates for the measurement area.

The measurement area determination unit 123 obtains information on the second expected received dose through the cassette control unit 112. The measurement area determination unit 123 compares the obtained second expected received dose with the dose detection signals of the detection pixels 65 situated in the irradiation field and the object area. The measurement area determination unit 123 determines the detection pixels 65 whose dose detection signals are within the predetermined confines (second expected received dose±α) centering on the second expected received dose, as the detection pixels 65 situated in the measurement area, being the region of interest. The determination of the irradiation field, the object area, and the measurement area (exclusion of the non-irradiation field and the directly exposed area from the candidates for the measurement area) is performed in real time on the dose detection signals outputted by the dose detection operation during making an exposure (during the accumulation operation of the FPD 45). The measurement area selection circuit 75 finally outputs to the integration circuit 76 the dose detection signals of the detection pixels 65 that are determined to be situated in the measurement area by the determination units 120, 121, and 123.

Note that, FIG. 9 shows a situation in which in the chest radiography, the irradiation field determination unit 120 excludes the dose detection signals of the detection pixels 65 situated in the non-irradiation fields at both ends of the imaging surface 47, and the object area determination unit 121 excludes the dose detection signals of the detection pixels 65 situated in the directly exposed areas between arms and an abdomen of the object M, and the measurement area determination unit 123 finally determines the detection pixels 65 situated in the right and left lung fields, being the measurement areas.

The determination units 120, 121, and 123 of the measurement area selection circuit 75 determine each of the above fields and areas, whenever the dose detection signals are sent from the detection pixels 65 at the predetermined sampling period. Otherwise, the determination as described above is performed on the dose detection signals that are sent first, and the first determination result is inherited thereafter.

Figure 10:
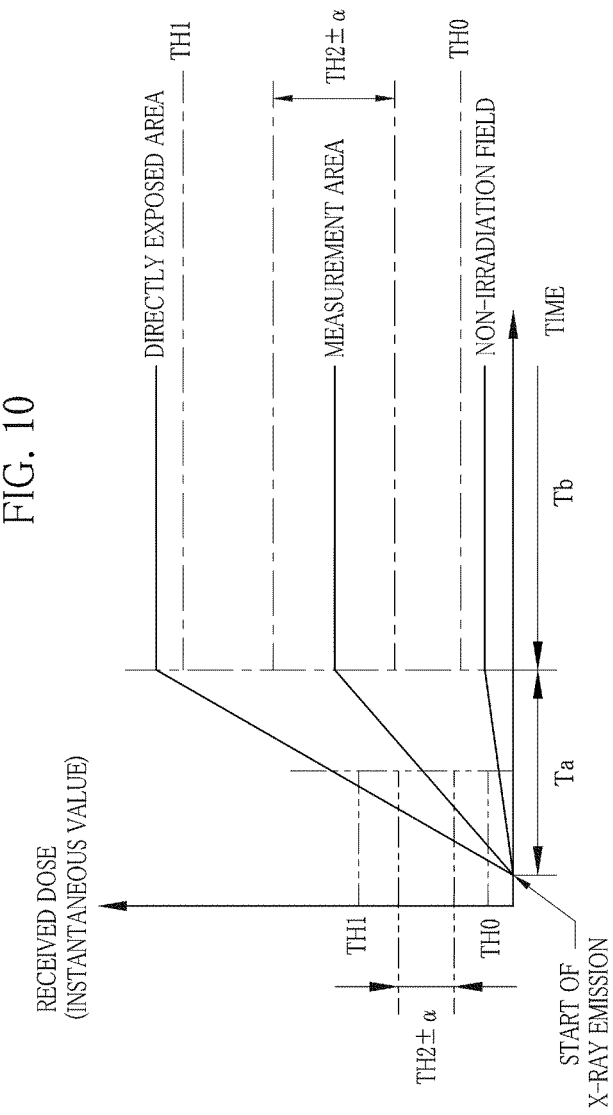
FIG. 10 is a diagram for explaining the timing of determining each area.

Specifically speaking, as shown in FIG. 10, the determination units 120, 121, and 123 of the measurement area selection circuit 75 can determine the irradiation field, the object area, and the measurement area in either of a period Ta in which the X-ray emission is started and the received dose is increasing, and a period Tb at which the operation of the X-ray source 10 becomes stable and the received dose is kept at a constant value corresponding to the set tube current. The manner of variation of the received dose is different from area to area in either period Ta, Tb, so it is possible to determine each area in either period without any problem.

In the case of determining each area in the period Ta in which the received dose is increasing, the dose detection signal is susceptible to noise because its value is relatively small. However, the determination of each area can be completed almost at the same time as the start of the X-ray emission, and hence the AEC is smoothly carried out.

In the case of determining each area in the period Tb in which the received dose is kept at the constant value, the dose detection signals obtained in the previous sampling are temporarily stored, and compared with the newly obtained dose detection signals. When the previous and new dose detection signals are equal to each other, the received dose is judged to be in the constant value, and the determination of each area is started. Although this case needs time for waiting until the received dose comes to the constant value, the dose detection signal is more stable and has a better S/N in the period Tb than in the period Ta, so it is possible to increase reliability of the determination result of each area.

Note that, as a matter of course, each of the threshold value TH0 for determining the non-irradiation field, the first expected received dose TH1, and the second expected received dose TH2 is set at different values between the case of determining each area in the period Ta and the case of determining each area in the period Tb. The values set in the period Ta, as shown by chain double-dashed lines, are smaller than the values set in the period Tb, as shown by chain single-dashed lines.

Figure 11:
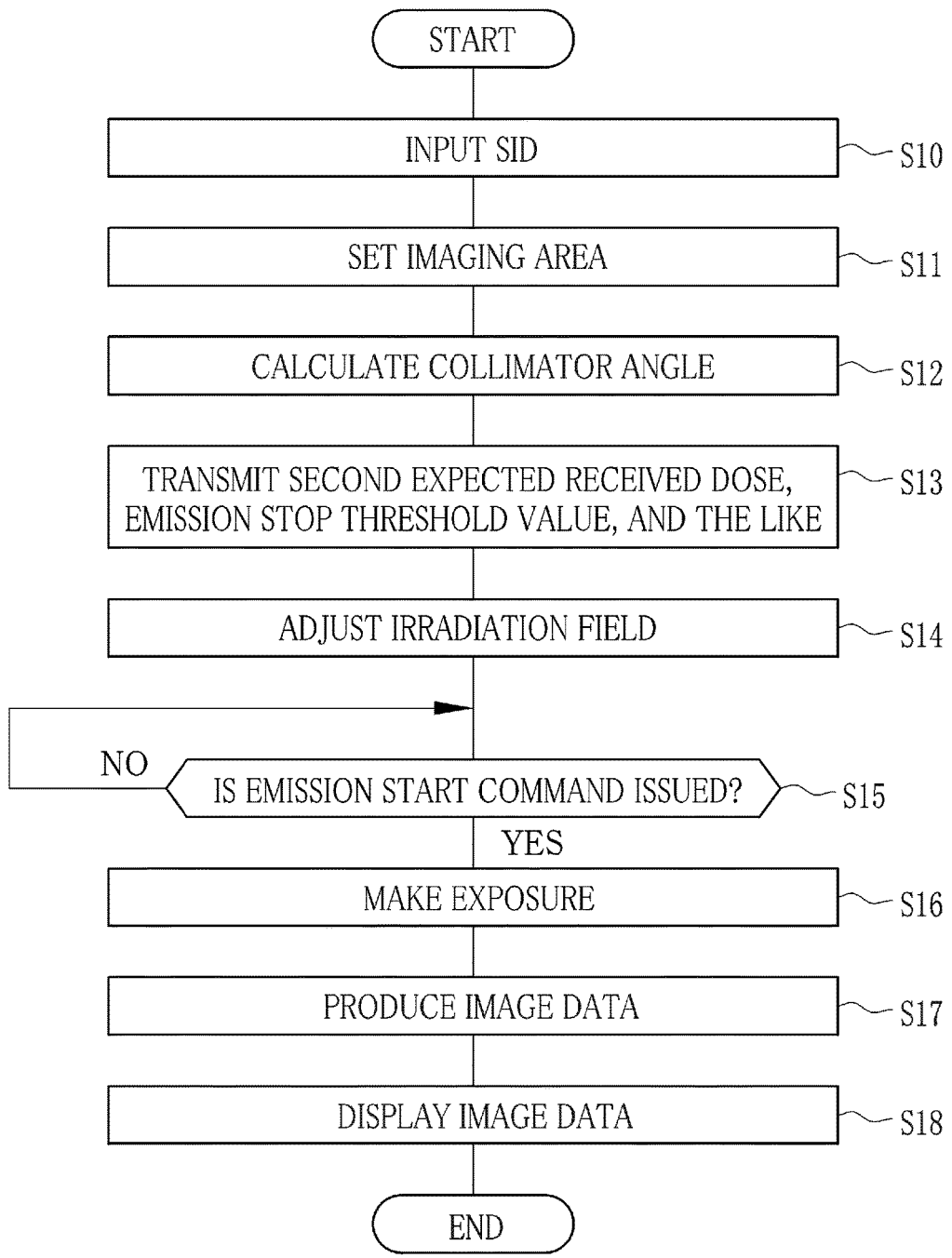
FIG. 11 is a flowchart of an X-ray imaging operation.
Figure 12:
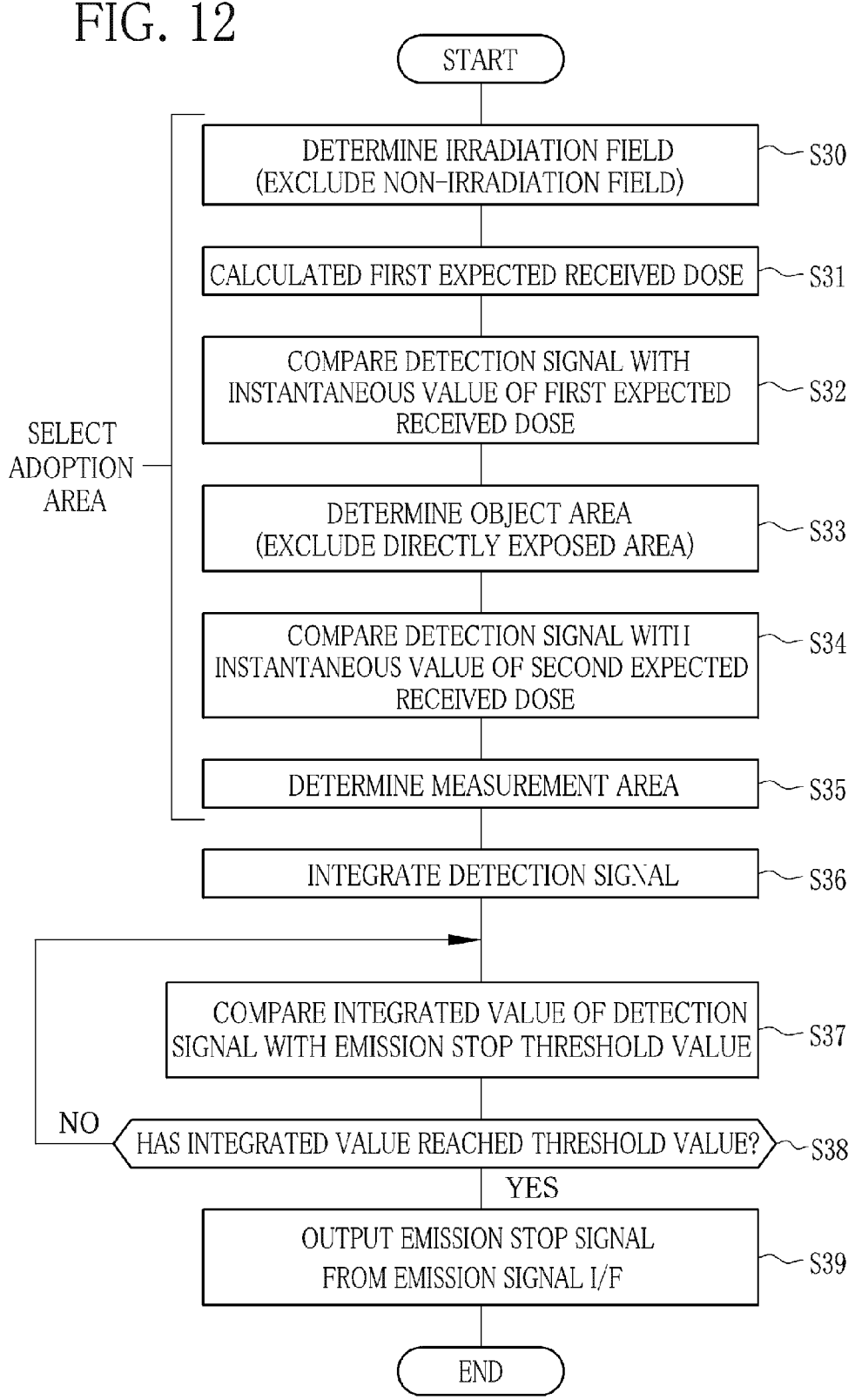
FIG. 12 is a flowchart of an AEC operation.

Next, a processing procedure of the X-ray imaging using the X-ray imaging system 2 will be described with referring to flowcharts of FIGS. 11 and 12. After the X-ray source 10 and the imaging stand 15 are disposed in an appropriate position, as shown in the step 10 (S10) of FIG. 11, the SID is measured and inputted to the console 14 from the input device 19. Then, the object M stands at a predetermined position in front of the imaging stand 15, and the widths $X_P$ and $Z_P$ of the imaging area are set (S11).

The step S10 may be omitted in a case where the SID is unvarying and inputted in advance, a case where the SID is determined according to a body part to be imaged and the imaging condition stored in the storage device 102 has a value of the SID of each body part in advance, or a case where a position sensor for detecting the horizontal of the X-ray source 10 and the imaging stand 15 is provided and the SID is automatically calculated based on output of the position sensor.

The measurement value of the SID, and the widths $X_P$ and $Z_P$ of the imaging area are inputted to the collimator angle setting unit 110. The collimator angle setting unit 110 calculates the collimator angles $\theta_X$ and $\theta_Z$ (S12). Information on the calculated collimator angles $\theta_X$ and $\theta_Z$ is outputted to the drive control unit 111.

Then, the imaging condition is set in the source control device 11 and the console 14. After setting the imaging condition, information about various parameters (the widths $X_P$ and $Z_P$ of the imaging area, the collimator angles $\theta_X$ and $\theta_Z$, the SID, the tube voltage, the tube current, and the like) required for determining the irradiation field and calculating the first expected received dose, the second expected received dose corresponding to the set body part to be imaged, and the emission stop threshold value is transmitted to the electronic cassette 13 through the cassette control unit 112 (S13).

Next, under the control of the drive control unit 111, the source control device 11 drives the irradiation field limiter 17 so as to adjust the irradiation field in accordance with the collimator angles $\theta_X$ and $\theta_Z$ calculated by the collimator angle setting unit 110 (S14).

After that, the X-ray imaging system 2 is put in a standby state waiting for the emission start command (S15). When the operator presses the emission switch 12 and the emission start command is issued (YES in S15), the X-ray source 10 starts emitting the X-rays. Concurrently with this, the FPD 45 starts the accumulation operation of the electric charge to make an exposure (S16).

Paralleling the accumulation operation of the FPD 45, the electronic cassette 13 carries out the AEC at its AEC unit 62 based on the output of the detection pixels 65. As shown in FIG. 12, the irradiation field determination unit 120 of the measurement area selection circuit 75 chooses the dose detection signals of the detection pixels 65 situated in the irradiation field of the X-rays in the imaging surface 47, out of the dose detection signals of the plurality of detection pixels 65 inputted from the A/D converter 59 (S30).

Then, the first expected received dose calculation unit 122 calculates the first expected received dose, that is, the X-ray dose to be received by the directly exposed area (S31). The object area determination unit 121 compares the calculated first expected received dose with the dose detection signals of the detection pixels 65 situated in the irradiation field (S32). The detection pixels 65 whose dose detection signals are the first expected received dose or more are determined to be situated in the directly exposed area, while the other detection pixels 65 are determined to be situated in the object area (S33). Note that, the calculation of the first expected received dose may be performed before starting the exposure, for example, when the imaging condition including the parameters required for the calculation is set.

Then, the measurement area determination unit 123 compares the second expected received dose with the dose detection signals of the detection pixels 65 that are situated in the irradiation field and the object area (S34). Thereby, the detection pixels 65 that are situated in the measurement area, being the region of interest, are determined (S35). The dose detection signal outputted from the detection pixel 65 that is determined to be situated in the measurement area is outputted to the integration circuit 76, and the integration circuit 76 integrates the signal (S36).

The threshold value generation circuit 78 generates the emission stop threshold value provided by the cassette control unit 112, and outputs the emission stop threshold value to the comparison circuit 77. The comparison circuit 77 compares the integrated value of the dose detection signal calculated by the integration circuit 76 with the emission stop threshold value (S37). As soon as the integrated value has reached the threshold value (YES in S38), the emission stop signal is outputted. The emission stop signal outputted from the comparison circuit 77 is transmitted from the emission signal I/F 80 to the emission signal I/F 35 of the source control device 11 (S39).

Upon receiving the emission stop signal by the emission signal I/F 35 of the source control device 11, the controller 31 stops electric power supply from the high voltage generator 30 to the X-ray source 10, and thereby the X-ray emission is stopped. In the electronic cassette 13, the FPD 45 shifts from the accumulation operation to the readout operation. The image data is outputted in the readout operation (S17 of FIG. 11).

The image data outputted from the FPD 45 is wiredly or wirelessly transmitted to the console 14 through the communicator 40. The image processing unit 113 applies various types of image processes to the image data. The display control unit 114 displays the processed image data on the display 20 (S18 of FIG. 11).

As described above, according to the present invention, the determination units 120, 121, and 123 of the measurement area selection circuit 75 determine the irradiation field, the object area, and the measurement area, respectively, and the dose detection signal of the detection pixel 65 that is determined to be situated in the measurement area is chosen. Therefore, it is possible to determine the measurement area in real time during making an exposure, and eliminate the need for making another exposure in advance for setting the measurement area or performing an image process such as a histogram analysis. Each area can be determined easily and speedily using simple calculation and comparison. The determination of each area can be completed in the period Ta in which the X-ray emission is started and the received dose is increasing.

If the detection pixels 65 that are determined to be situated in the measurement area include one that is actually situated in the non-irradiation field or the directly exposed area, the AEC may not be carried out appropriately. However, the irradiation field determination unit 120 and the object area determination unit 121 reliably excludes the detection pixel 65 that is situated in the non-irradiation field or the directly exposed area, the reliability of the AEC is increased.

Stepwise narrowing the candidates for the measurement area via the steps of the irradiation field, the object area, and the measurement area increases the appropriateness of the determination result of the detection pixels 65, as compared with the case of determining the measurement area directly from the entire imaging surface 47. The reliability of the AEC is further improved.

Second Embodiment

Note that, the present invention may be applied to continuous imaging as will be described in this embodiment, in addition to the imaging of one body part such as the chest or the abdomen using the X-ray source and the electronic cassette fixed in certain positions, as described in the first embodiment. Note that, a component having the same structure and function as the component of the first embodiment has is indicated with the same reference numeral, and detailed description thereof will be omitted.

Figure 13:
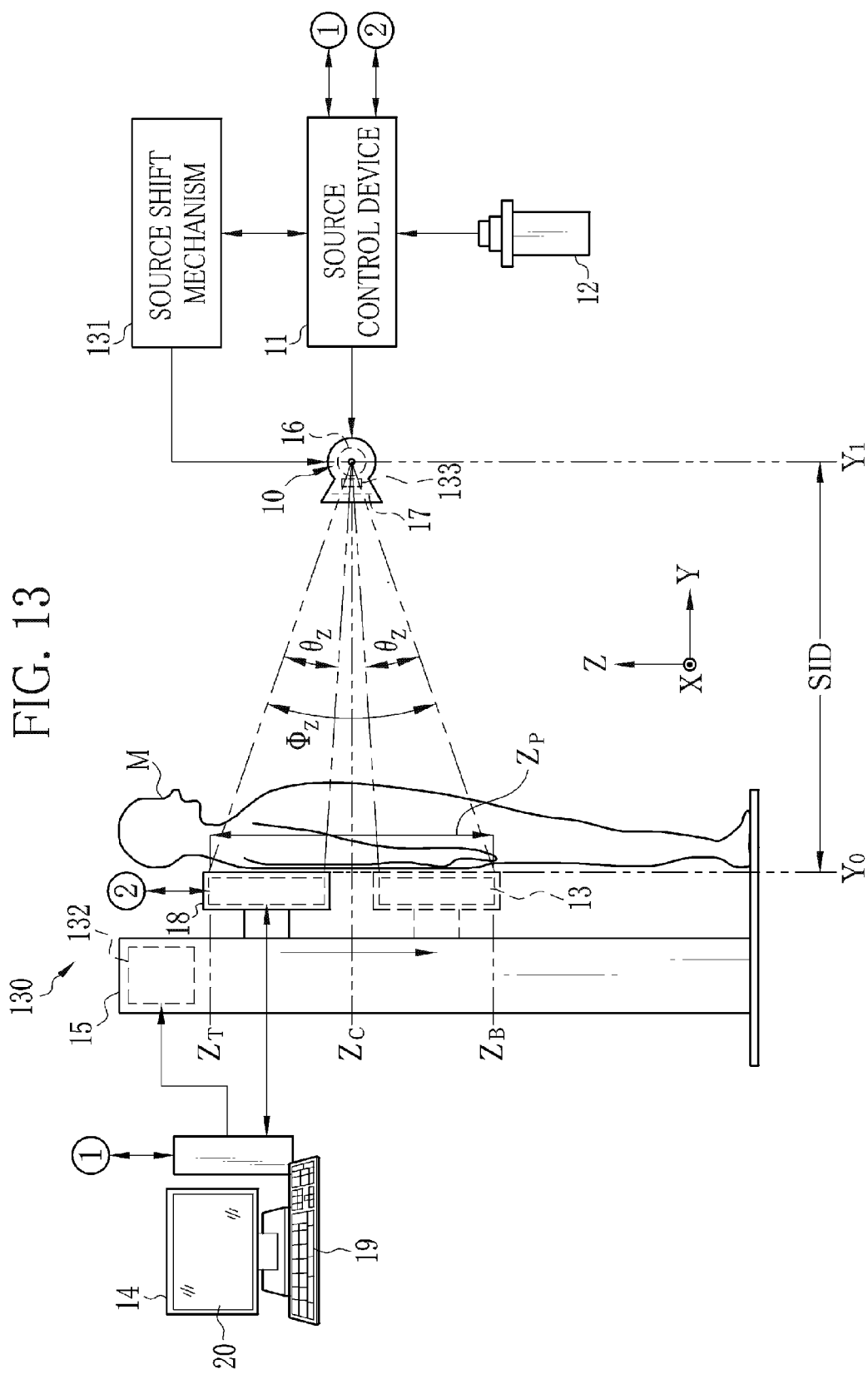
FIG. 13 is a schematic view showing the structure of an X-ray imaging system that can perform continuous imaging.

In FIG. 13, an X-ray imaging system 130 has structure that enables the continuous imaging. The source control device 11 controls the operation of a source shift mechanism 131 so as to turn the X-ray source 10 with following a vertical shift of the holder 18 of the imaging stand 15 in the continuous imaging. The source shift mechanism 131 includes an arm that is extendable in the Z direction and hangs the X-ray source 10 from a ceiling and has the function of turning the X-ray source 10 in the Z direction, a rail that is attached to the arm and shifts the X-ray source 10 together with the arm in an XY direction, and a driving source such as a motor. The position of the X-ray source 10 can be changed automatically under the control of the source control device 11, or manually by the operator such as a radiological technician. In the continuous imaging, the X-ray source 10 is shifted such that the height of the X-ray source 10 corresponds to the center $Z_C$ of the imaging area of the object M in the Z direction.

The imaging stand 15 is provided with a holder shift mechanism 132 that allows the vertical shift of the holder 18 in the Z direction without changing an orientation of the imaging surface 47 of the FPD 45 of the electronic cassette 13. The holder shift mechanism 132 can change the position (height) of the holder automatically under the control of the console 14, or manually by the operator.

The X-ray source 10 has a laser source 133. The laser source 133 is turned on when setting the imaging area of the object M. The laser source 133 emits two types of linear laser beams that are parallel to the X and Z directions, respectively, in front of the X-ray source 10.

The operator makes the object M stand at a predetermined position in front of the imaging stand 15, and operates the touch panel 34 of the source control device 11 to turn on the laser source 133. Then, as shown in FIGS. 14(A) and (B), the height of the X-ray source 10 is set by the operation of the source shift mechanism 131 in such a position that the linear laser beam parallel to the X direction coincides with a top end $Z_T$ of the desired imaging area, in order to set the height $Z_P$ of the imaging area in the Z direction. After that, the X-ray source 10 is turned downwardly in the Z direction such that the linear laser bean parallel to the X direction coincides with a bottom end $Z_B$ of the desired imaging area. As for the width $X_P$ of the imaging area in the X direction, in a like manner, while the linear laser beam parallel to the Z direction is emitted, the X-ray source 10 is turned horizontally such that the linear laser beam is applied to a desired position. However, right and left turn angles in the X direction are equal to each other with respect to their center. At this time, a potentiometer contained in the source shift mechanism 131 detects the height (=$Z_T$) of the X-ray source 10 in the Z direction and the turn angles $\phi_X$ and $\phi_Z$. A detection result of the potentiometer is transmitted from the source control device 11 to the console 14 whenever the touch panel 34 is operated. Note that, $Z_P$, $Z_T$, and $Z_B$ of FIG. 13 indicate an example of the imaging area in the Z direction in the case of imaging a full spine, and almost covers an upper body extending from a thorax to a waist (a pelvis) of the object M.

In the above example, after the height of the X-ray source 10 is made flush with the top end $Z_T$ of the desired imaging area, the X-ray source 10 is turned downwardly in the Z direction to set the bottom end $Z_B$. However, the bottom end $Z_B$ may be set first, and then the X-ray source 10 may be turned upwardly in the Z direction to set the top end $Z_T$. Also, as shown in FIG. 14(C) the X-ray source 10 disposed in an arbitrary height may be turned upwardly and downwardly in the Z direction to set the top end $Z_T$ and the bottom end $Z_B$. The imaging area may be set based on the height of the X-ray source 10 and turn angles $\phi'_Z$ and $\phi''_Z$ thereby.

Figure 15:
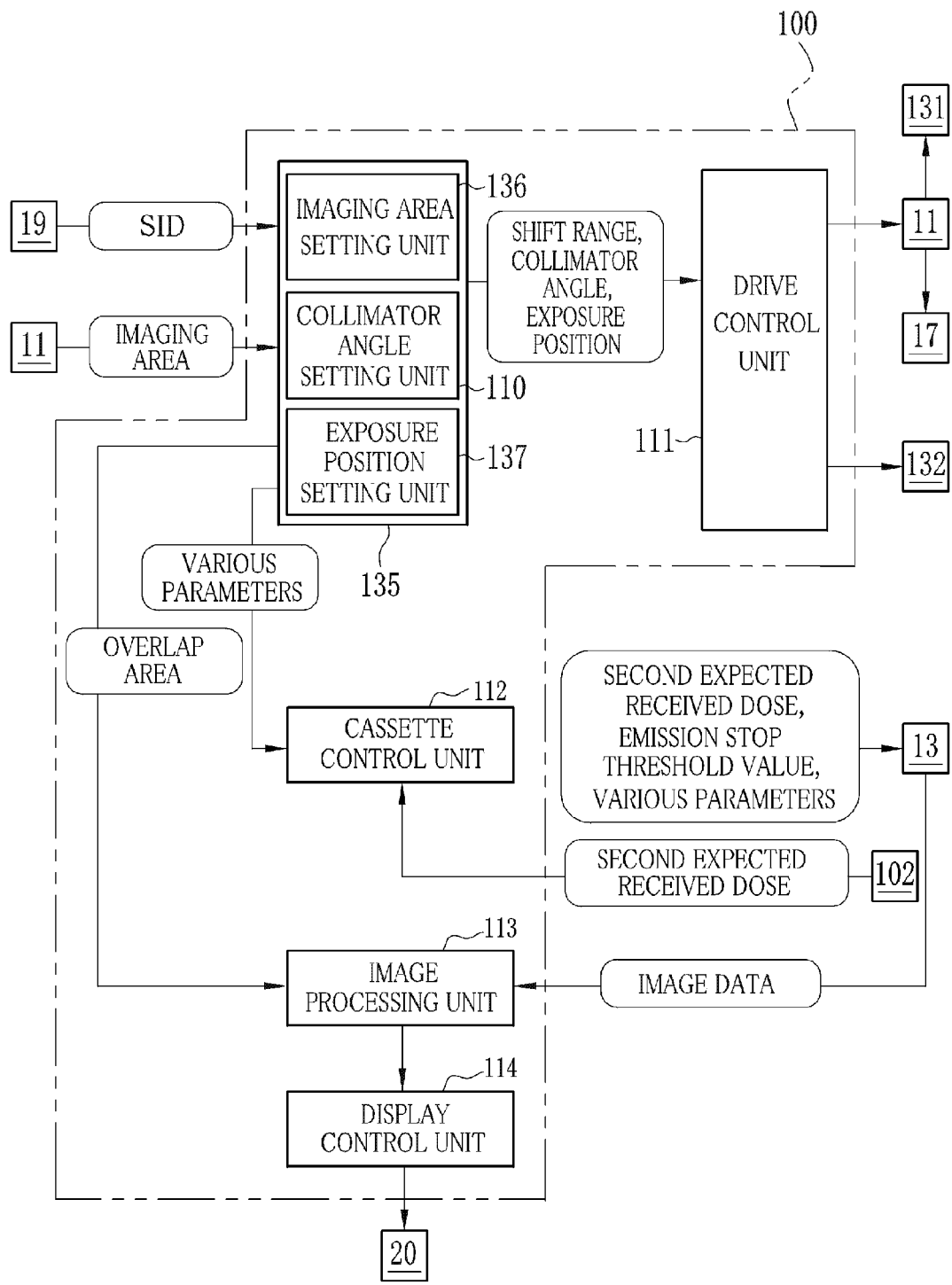
FIG. 15 is a block diagram showing the function of the console and an information flow in the continuous imaging.

In FIG. 15, when executing the AP 105 and choosing the continuous imaging, a driving condition setting unit 135 is configured in the CPU 100 of the console 14, in addition to the drive control unit 111, the cassette control unit 112, and the like of the first embodiment. The driving condition setting unit 135 sets not only the collimator angle of the emission field limiter 17, but also a shift range of the holder 18, a turn angle range of the X-ray source 10, and exposure positions within the shift range in the continuous imaging. In accordance with various types of driving conditions set by the driving condition setting unit 135, the drive control unit 111 drives the source shift mechanism 131 and the irradiation field limiter 17 via the source control device 11, and drives the holder shift mechanism 132. The image processing unit 113 collects image data obtained in each exposure position and produces longitudinal image data by merging, after applying various types of image processes such as the offset correction, the gain correction, and the defect correction to the image data, as described above. The display control unit 114 displays a merged X-ray image (longitudinal image) based on the longitudinal image data on the display 20.

The driving condition setting unit 135 includes an imaging area setting unit 136 for setting the shift range of the holder and the turn angle range of the X-ray source 10, and an exposure position setting unit 137 for setting the exposure positions within the above shift range, in addition to the collimator angle setting unit 110 of the first embodiment.

The imaging area setting unit 136 calculates the width $X_P$ and the height $Z_P$ of the imaging area, based on the SID inputted through the input device 19 and the detection result (the top end $Z_T$ and the turn angles $\phi_X$ and $\phi_Z$) of the potentiometer in setting the imaging area using the laser source 133 that is inputted from the source control device 11. More specifically, the following expressions (3-1) and (3-2) are calculated (refer to FIG. 14):

$$X_P = 2 \times SID \times \tan(\theta_X/2) \qquad \text{Expression (3-1)}$$

$$Z_P = SID \times \tan \phi_Z \qquad \text{Expression (3-2)}$$

From the calculation results, the bottom end $Z_B$ and the center $Z_C$ of the imaging area in the Z direction are obtained. The imaging area setting unit 136 sets the top end $Z_T$ and the bottom end $Z_B$ of the imaging area in the Z direction as the shift range of the holder 18, and sets the center $Z_C$ as the position of the X-ray source 10 in the continuous imaging. In the case of full spine imaging, the holder shift mechanism 132 shifts the holder 18 between a shift start position set at the bottom end $Z_B$ and a shift end position set at the top end $Z_T$. In the case of lower limb imaging, the top end $Z_T$ is set as the shift start position, and the bottom end $Z_B$ is set as the shift end position. Thus, in either of the full spine imaging and the lower limb imaging, a waist is imaged at first.

The imaging area setting unit 136 calculates from the following expression (4) the turn angle range $\Phi_Z$ (see FIG. 13) of the X-ray source 10 in the case of disposing the X-ray source 10 at the center $Z_C$ of the imaging area in the Z direction:

$$\Phi_Z = 2 \times \tan^{-1}\{(Z_P/2)/SID\} \qquad \text{Expression (4)}$$

The source shift mechanism 131 changes the turn angle $\phi_Z$ of the X-ray source 10 in the Z direction to the above turn angle range $\Phi_Z$ so that the turn of the X-ray source 10 synchronizes with the vertical shift of the holder 18.

Figure 16:
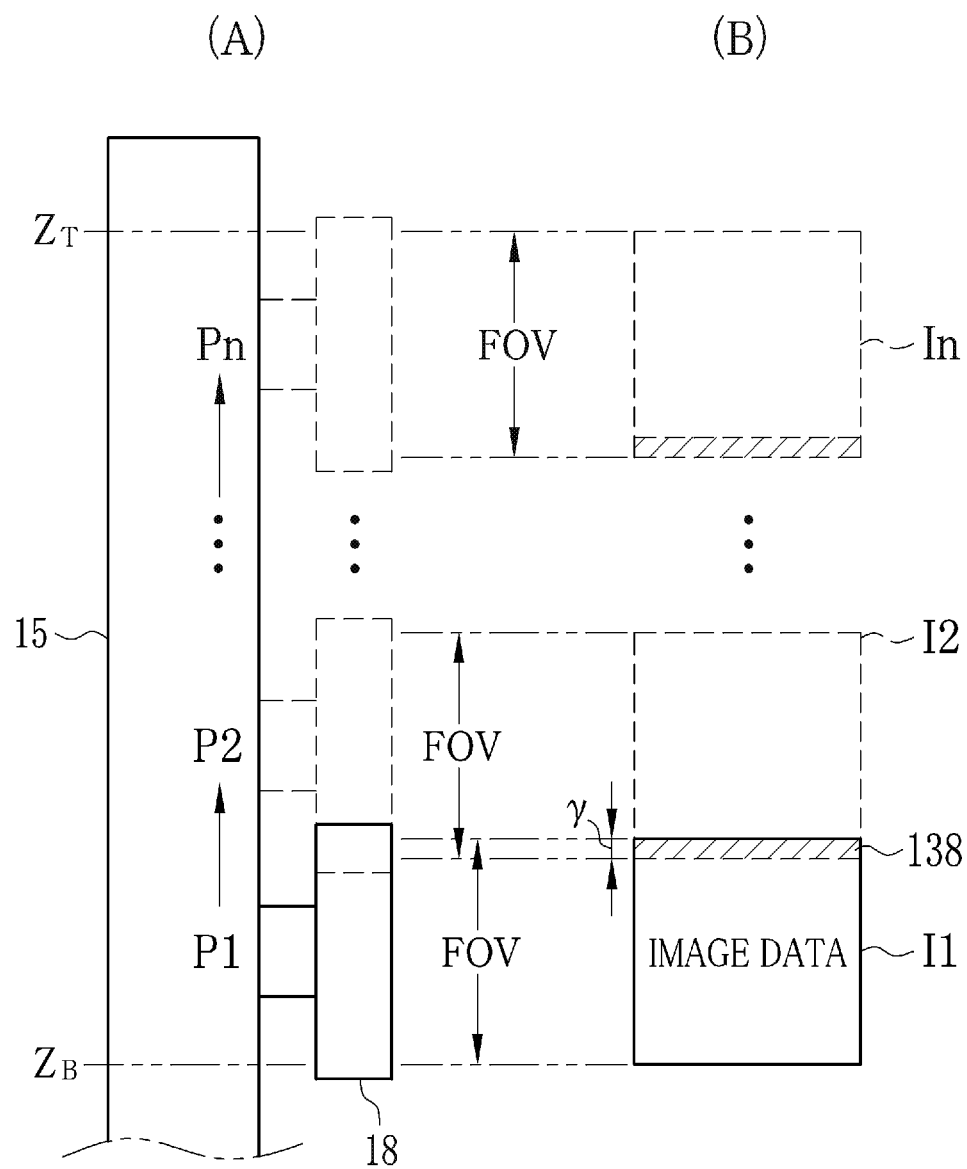
FIG. 16 is a diagram showing a state of the continuous imaging, and (A) shows each exposure position in the continuous imaging, and (B) shows image data obtained in each exposure position.

The collimator angle setting unit 110 calculates the collimator angles in the continuous imaging based on the SID, the length FOV (field of view) of the imaging surface 47 of the FPD 45 in the Z direction (see FIG. 16), and the width $X_P$ of the imaging area. The collimator angle $\theta_X$ in the X direction is calculated from the expression (1-1), as in the case of the first embodiment. The collimator angle $\theta_Z$ in the Z direction is calculated from the following expression (1-2)':

$$\theta_Z = 2 \times \tan^{-1}\{(FOV/2)/SID\} \qquad \text{Expression (1-2)'}$$

The collimator angle $\theta_X$ is common in each exposure position. On the other hand, the collimator angle $\theta_Z$ is an angle in a case where the height of the center of the X-ray source 10 and the imaging surface 47 in the Z direction coincides with the center $Z_C$, and hence corrected in accordance with a deviation between the height of the center of the imaging surface 47 in the Z direction and the center $Z_C$. In the continuous imaging, the source control device 11 drives the irradiation field limiter 17 such that the collimator angles $\theta_X$ and $\theta_Z$ coincide with values obtained by the above expressions (1-1) and (1-2)', respectively, or the corrected values.

The exposure position setting unit 137 set each exposure position in the continuous imaging, based on the height $Z_P$ of the imaging area and the length FOV of the imaging surface 47 in the Z direction. Specifically speaking, the following expression (5) is calculated at first:

$$Z_P/FOV \qquad \text{Expression (5)}$$

In order to overlap the imaging surface 47 between the adjoining exposure positions, 1 is added to a quotient in a case where a calculation result of the above expression (5) is an integer. In a case where the calculation result is not an integer, the fractional portion of the calculation result is rounded up to calculate the number n of making exposures. After the number n of exposures is determined, as shown in FIG. 16(A), the shift start position (the first exposure position) 51 in which the bottom end of the imaging surface 47 coincides with the bottom end $Z_B$, and the shift end position (the n-th exposure position) Pn in which the top end of the imaging surface 47 coincides with the top end $Z_T$ are determined (in the case of the full spine imaging. Opposite in the case of the lower limb imaging). A distance between the shift start position P1 and the shift end position Pn is equally divided by a number of (n−1), and obtained positions are assigned as the other exposure positions.

For example, in the case of $Z_P$=100 cm and FOV=25 cm, $Z_P$/FOV=4 being an integer, so the number of exposures is calculated at "5" by 4+1. The distance d=18.75 cm between the adjoining two exposure positions out of the exposure positions P1, P2, P3, P4, and P5. In the case of $Z_P$=100 cm and FOV=30 cm, $Z_P$/FOV=3.33 . . . being not an integer. Rounding up the fractional portion, the number of exposures is calculated at "4". The distance d≈23.3 cm between the adjoining two exposure positions out of the exposure positions P1, P2, P3, and P4.

FIG. 16(B) shows image data I1 to In obtained in each of the exposure positions P1, P2, . . . , Pn. There is an overlap area 138 between the image data of adjoining exposure positions, due to an overlap of the imaging surface 47 between the adjoining exposure positions. This overlap area 138 facilitates producing the longitudinal image data by the image processing unit 113 without chipping the image data. The overlap amount γ of the overlap area 138 is calculated by the following expression (6):

$$\gamma = \{n \times FOV - Z_P\}/(n-1) \qquad \text{Expression (6)}$$

In the case of $Z_P$=100 cm and FOV=25 cm, γ=(5×25−100)/2=12.5 cm. In the case of $Z_P$=100 cm and FOV=30 cm, γ=(4×30−100)/3≈6.7 cm.

The exposure position setting unit 137 outputs information about the shift start position, the shift end position, the calculated number n of exposures, and the distance d between the adjoining exposure positions to the drive control unit 111. Under the control of the drive control unit 111, the holder shift mechanism 132 sequentially shifts the holder 18 in the Z direction from the exposure position P1 to the exposure position Pn at the distance d. The source control device 11 controls the operation of the source shift mechanism 131 such that the X-ray source 10 turns at the turn angle $\Phi_Z$ so as to make the irradiation field of the X-rays coincide with the imaging area of each exposure position. The source control device 11 controls the operation of the X-ray source 10, such that the X-rays are emitted after the holder 18 is shifted and stopped at each exposure position and the X-ray source 10 is turned by the desired turn angle $\phi_Z$.

The exposure position setting unit 137 outputs information about the calculated overlap amount γ of the overlap area 138 to the image processing unit 113. Based on the information on the overlap amount γ, the image processing unit 113 joins the image data obtained in each exposure position at the overlap area 138 to produce the longitudinal image data.

In this case, an AEC unit has almost the same structure as the AEC unit 62 of the first embodiment. However, the irradiation field determination unit 120 determines the irradiation field of the X-rays in the imaging surface 47, which is determined by the exposure position and the turn angle $\phi_Z$ of the X-ray source 10 in addition to the collimator angles $\theta_X$ and $\theta_Z$ and the SID. Note that, one type of second expected received dose, corresponding to the region of interest, is stored with respect to each body part to be imaged in the first embodiment. However, the region of interest may be divided into small portions, such that the body part of the full spine is divided into two portions of a waist and a spine, or the body part of the lower limb is divided into three portions of a waist, knees, and ankles, and the second expected received dose may be stored from portion to portion. In this case, in the full spine imaging, the cassette control unit 112 provides the second expected received dose of the waist at the first exposure and the second expected received dose of the spine at the second or later exposures. In the case of the lower limb imaging, the cassette control unit 112 provides the second expected received dose of the waist at the first exposure, the second expected received dose of the knees at the second exposure, and the second expected received dose of the ankles at the third exposure for the electronic cassette 13.

Figure 17:
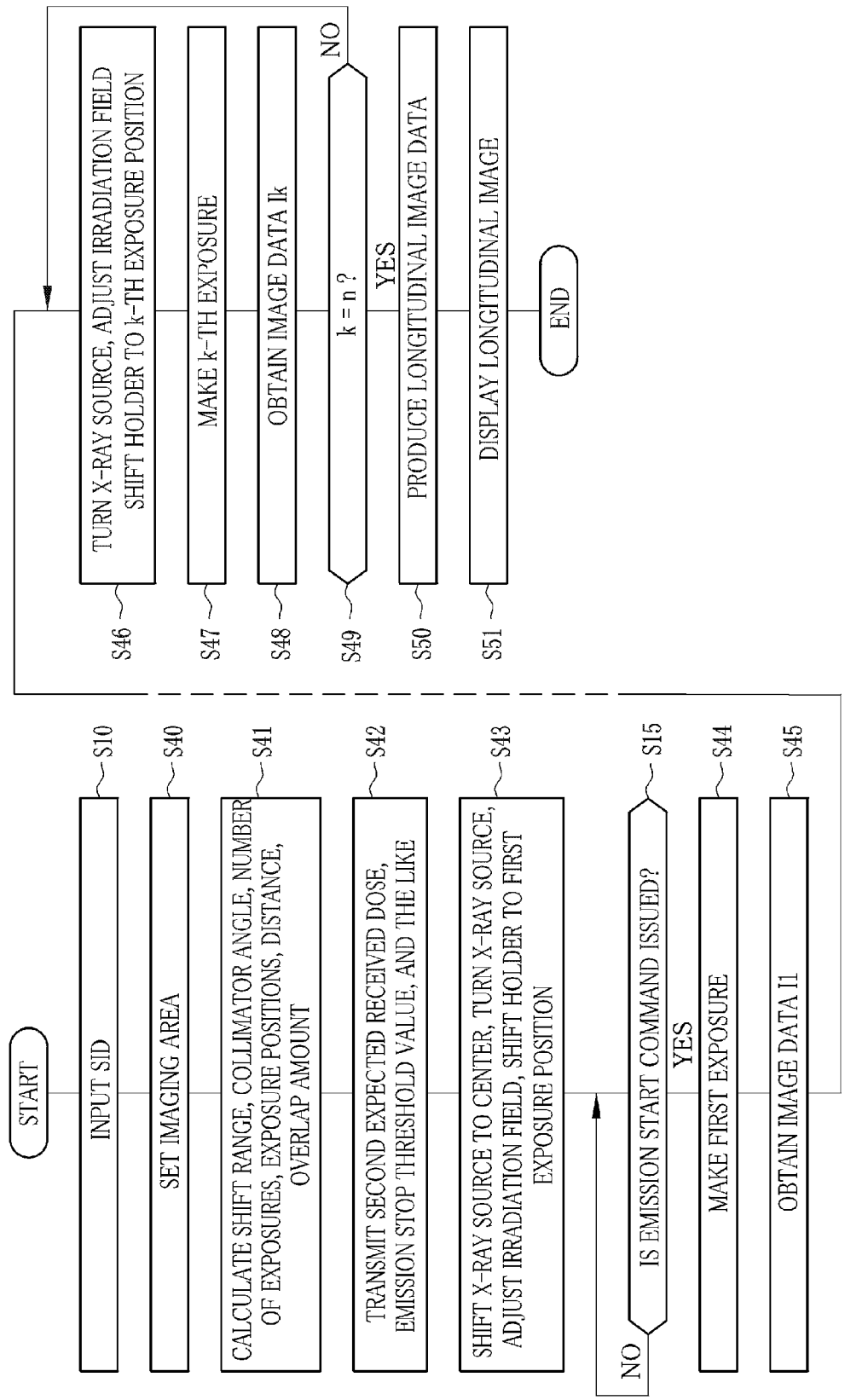
FIG. 17 is a flowchart of a continuous imaging operation.

Next, a processing procedure of the continuous imaging (full spine imaging) using the X-ray imaging system 130 will be described with referring to a flowchart of FIG. 17. The same step as the first embodiment has is indicated with the same reference numeral, and detailed description thereof will be omitted.

After the SID is inputted at S10, the object M stands at the predetermined position in front of the imaging stand 15. In this state, the laser source 133 is turned on. The source shift mechanism 131 adjusts the height of the X-ray source 10 and turns the X-ray source 10 in the Z direction or the X direction, to set the imaging area (S40). The measurement value of the SID, and the height (top end $Z_T$) and the turn angles $\phi_X$ and $\phi_Z$ of the X-ray source 10 detected by the potentiometer are inputted to the driving condition setting unit 135. The driving condition setting unit 135 calculates the shift range, the collimator angle θ, the number n of the exposures, the exposure positions P1, P2, . . . , Pn and the distance d therebetween, the overlap amount γ of the overlap area 138, and the like using the imaging area setting unit 136, the collimator angle setting unit 110, and the exposure position setting unit 137 (S41). This information is outputted to the drive control unit 111 and the like.

When the driving condition is set and the imaging condition is set in the source control device 11 and the console 14, information about various parameters including the turn angle $\phi_Z$ of the X-ray source 10 in addition to the widths $X_P$ and $Z_P$ of the imaging area, the collimator angles $\theta_X$ and $\theta_Z$, the SID, the tube voltage, and the tube current as described in the first embodiment, the second expected received dose, the emission stop threshold value, and the like is transmitted to the electronic cassette 13 through the cassette control unit 112 (S42).

Then, under the control of the drive control unit 111, the source shift mechanism 131 and the holder shift mechanism 132 are driven. The X-ray source 10 is shifted to the center $Z_C$ and turned by a turn angle of the first exposure, while the holder 18 is shifted to the first exposure position P1. The source control device 11 drives the emission field limiter 17, such that the irradiation field has the collimator angles $\theta_X$ and $\theta_Z$ calculated by the collimator angle setting unit 110 (S43).

When the operator presses the emission switch 12 and the emission start command is issued (YES in S15), the X-ray source 10 starts emitting the X-rays. Concurrently with this, the FPD 45 starts the accumulation operation of the electric charge to make the first exposure (S44). The first exposure captures the image data I1 (S45). The operation of the AEC unit at this time is the same as that of the first embodiment as shown in FIG. 12.

Similarly, while the holder 18 is shifted to the k-th exposure position Pk (k=2, 3, 4, . . . , n), the X-ray source 10 is turned by the desired turn angle $\theta_Z$ with adjusting the irradiation field (S46). The k-th exposure is made with setting the measurement area determined by the measurement area selection circuit 75 (S47), and thereby the image data Ik is obtained (S48). The above steps are repeated until the number of the exposures reaches n (k=n, YES in S49).

After completing the n-th exposure, the image processing unit 113 performs a merging step in which the image data I1, I2, . . . , In obtained in each exposure position P1, P2, . . . Pn is joined at the overlap area 138 to produce the single longitudinal image data (S50). The display control unit 114 displays the produced longitudinal image data on the display 20 (S51).

This embodiment can obtain the same effect as the first embodiment do. This invention is preferably applicable to the continuous imaging, which has to make a plurality of exposures continuously and quickly so as to prevent displacement in the merged image due to body movement of the object M, because the present invention allows determination of the measurement area in real time during making the exposures and eliminates the need for making another exposure in advance for setting the measurement area or performing an image process such as a histogram analysis.

In the second embodiment, the waist is imaged at the first exposure in both of the full spine imaging and the lower limb imaging. This is because the waist having a pelvis tends to be the most noteworthy in making a diagnosis. However, the present invention is not limited to this, a portion other than the waist may be imaged at first. For example, in the case of an examination of knee arthropathy, the knees are assigned as a portion to be imaged at the first exposure.

As a way to set the imaging area, a method other than one described above may be used. For example, instead of the laser source 133, a visible light source that applies rectangular visible light to the object M through the irradiation field limiter 17 may be provided. In this case, the collimator angles $\theta_X$ and $\theta_Z$ are adjusted such that an area irradiated with the rectangular visible light coincides with the desired imaging area, and the size of the imaging area is calculated based on a geometrical expression having the adjusted collimator angles $\theta_X$ and $\theta_Z$ and the SID. Otherwise, the holder 18, instead of the X-ray source 10, may have a sight such as the laser source 133. Instead of providing the sight or the like, the size of the imaging area may be measured by a ruler, and the measurement value may be inputted from the input device 19.

Increase in a ratio of the overlap amount γ to the length FOV of the imaging surface 47 in the Z direction causes increase in radiation exposure of the object M at the overlap area 138, so it is preferable to set a ceiling on the overlap amount γ (for example, a length of 10% of the FOV). Comparing the overlap amount γ calculated by the above expression (6) with the predetermined ceiling value, in a case where the overlap amount γ is larger than the ceiling value, the exposure positions P1, P2, . . . , Pn are slid equally in a vertical direction such that the overlap amount γ comes to the ceiling value.

The overlap amount γ may be always constant. In this case, the imaging surface 47 may extend off the imaging area at the n-th exposure. In this case, the irradiation field of the X-rays is made small in accordance with the top end or the bottom end of the imaging area.

The second embodiment describes the case of using the imaging stand in which the holder 18 is shifted in the vertical direction with respect to the standing object M, as an example, but the present invention is not limited to this. The present invention is applicable to imaging in which the holder is shifted to a horizontal direction with respect to the object M lying on an imaging bed. The holder 18 is shifted along a body axis of the object M in the second embodiment, but may be shifted in a different direction from the body axis of the object M in the continuous imaging.

The second embodiment adopts a turning method by which the angle of the X-ray source is changed so as to change an X-ray emission direction in accordance with the shift of the holder 18 loaded with the electronic cassette 13. However, the present invention may be applied to a linear shift method by which the X-ray source 10 is linearly shifted in accordance with the shift of the holder loaded with the electronic cassette. Furthermore, the exposures may be made while shifting the holder 18 and the X-ray source 10 without stopping them at each exposure position.

The present invention is applicable to any type of X-ray imaging performing the AEC, including stereo imaging in which the X-ray imaging is performed using two X-ray sources located in different positions to obtain two images having parallax and enable stereo imaging of an X-ray image based on the two images, tomosynthesis imaging in which X-rays are applied from a shifting X-ray source to an object at different angles and captured images are added to obtain a tomographic image having a desired emphasized tomographic surface, in addition to normal imaging for imaging a single body part such as a chest or an abdomen using the X-ray source and the electronic cassette fixed in one position as described in the first embodiment, and continuous imaging according to the second embodiment.

When the object area determination unit 121 compares the instantaneous value of the first expected received dose with the dose detection signals of the detection pixels 65 situated in the irradiation field, or when the measurement area determination unit 123 compares the instantaneous value of the second expected received dose with the dose detection signals of the detection pixels 65 situated in the irradiation field and the object area, the dose detection signals may not be compared one by one to determine the object area or the measurement area. Instead, the imaging surface 47 may be divided into a plurality of blocks, and a typical value of the dose detection signals of the plurality of detection pixels 65 contained in each block may be compared with the first or second expected received dose, to determine whether or not each block is included in the object area or the measurement area. The block is an area into which the imaging surface 47 is equally divided, for example. Each block has the plurality of detection pixels 65 that are near to each other. An average value of the dose detection signals of the plurality of detection pixels 65 contained in the block is calculated on a block-by-block basis, and the average value is compared with the first or second expected received dose as the typical value of the block. This reduces the number of time of the comparison and hence facilitates saving processing time, as compared with the case of making the comparison of the dose detection signals one by one. Note that, a maximum value, a mode value, or a sum value may be used instead of the average value as the typical value of the plurality of the dose detection signals of each block. In the case of using the sum value, a corrected value of the first or second expected received dose in accordance with the number of the dose detection signals contained in one block is set to make a comparison with the sum value.

A candidate area of the measurement area may be set in advance in each body part to be imaged, or may be set by the operator. The candidate area is an area that is supposed to have the measurement area. In the above embodiment, in the case of the chest radiography, the candidate area is an area that is supposed to have the lung fields, being the region of interest. Since the anatomical structure, e.g. the position of the lung fields of the object is almost fixed, though there are variations among individuals, an approximate area including the measurement area can be estimated. Such an area is set as the candidate area.

In the case of setting the candidate areas on a body part basis, for example, the candidate areas are set through the input device 19 and the display 20 of the console 14, and recorded to the storage device 102 with being associated with the body parts. In designating the body part to be imaged in each imaging operation, the candidate area is provided for the measurement area selection circuit 75 of the electronic cassette 13. Instead of recording the candidate areas in advance to the storage device 102, the candidate area may be set by judgment of the operator in each imaging operation. In this case, a schematic view of the imaging surface 47 is displayed on the display 20 of the console 14, and the operator designates a part of the schematic view through the input device 19 to set the candidate area. The set candidate area is provided for the measurement area selection circuit 75. Thus, the console 14 composes a candidate area setting unit.

In the case of setting the candidate area, the measurement area selection circuit 75 determines the irradiation field, the object area, and the measurement area within the candidate area. Otherwise, since it is conceivable that the candidate area does not include the non-irradiation field and the directly exposed area, only the determination of the measurement area may be performed, by skipping the determination of the irradiation field and the object area.

In a case where the detection pixel 65 of the electronic cassette 13 fails or the communication between the source control device 11 and the electronic cassette 13 fails due to a break in a wire or the like, the emission stop signal could not be transmitted appropriately and the AEC could not work. Especially, a maximum value of the tube current-emission time product is set in the source control device 11 as the imaging condition, so the malfunction of the AEC causes the patient to receive excessive radiation exposure of an upper limit or more. For this reason, the electronic cassette 13 has a test mode in which test imaging is performed with every exposure condition prepared in the console 14 immediately after installation or at the start of a day. The detection pixels 65 continue detecting the X-rays even after the electronic cassette 13 issues the emission stop signal to the source control device 11. In a case where a stop of the X-ray emission is detected within a predetermined time, the AEC is judged to work normally. If not, it is judged that any failure occurs, and a warning message is displayed on the display 20.

In a case where the emission signal I/Fs 35 and 80 of the source control device 11 and the electronic cassette 13 are connectable in both of wired and wireless methods, if wireless communication is judged to be unstable by a result of monitoring radio field intensity or the like, a warning to recommend switching to the wired method may be displayed.

In each of the above embodiments, the detection pixel 65 that is directly connected to the signal line 51 without interposition of the TFT 49 is used as the AEC sensor. However, as shown in an FPD 140 of FIG. 18, a detection pixel 141 may be connected to a TFT 144 that is driven by a gate driver 142 and a scan line 143 different from those for driving the normal pixels 46, so that accumulated electric charge can be read out independently of the normal pixels 46.

In each of the above embodiments, there are the pixels 46 for image detection and the detection pixels 65 functioning as the AEC sensors independently of each other. Thus, the defect correction is required by which the pixel values of a column having the detection pixel 65 are interpolated with the pixel values of an adjacent column having no detection pixel. This may cause deterioration in the image quality of the X-ray image.

Figure 19:
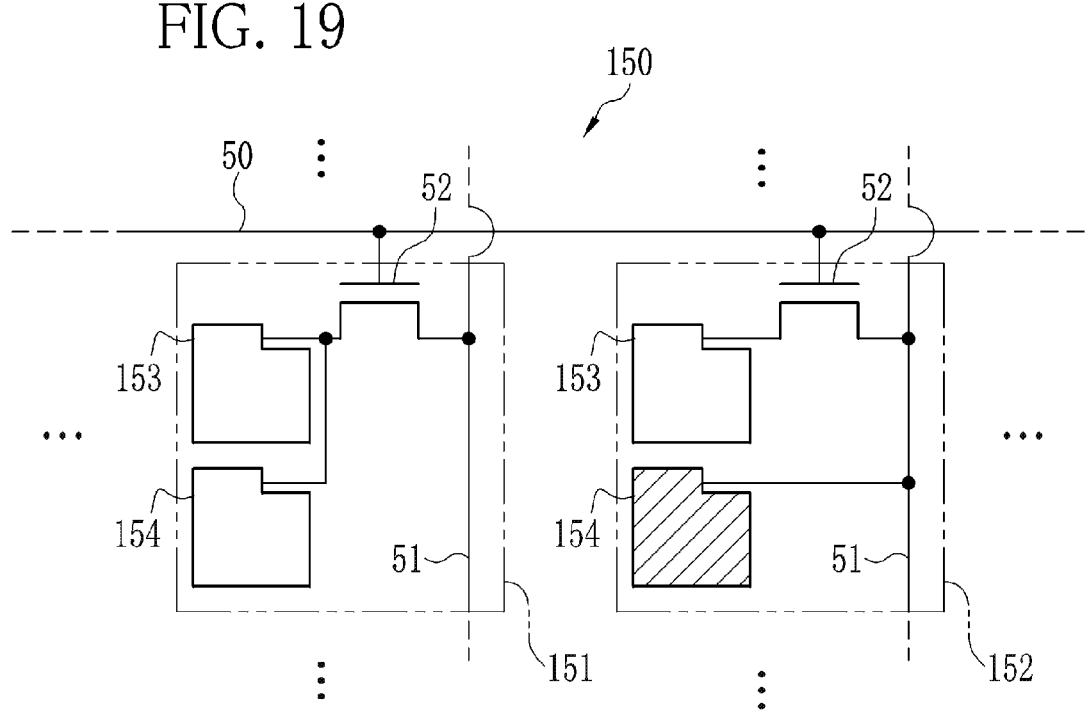
FIG. 19 is a diagram of an FPD of further another embodiment.

Accordingly, an FPD 150 having the structure of FIG. 19 eliminates the need for the defect correction based on the pixel values of the adjacent pixels.

In FIG. 19, the FPD 150 includes first pixels 151 dedicated to image detection and second pixels 152 for use in both of the image detection and the AEC. The first and second pixels 151 and 152 are arranged into a matrix at an appropriate ratio, as with the pixels 46 and the detection pixels 65 of the above embodiments. Each of the first and second pixels 151 and 152 has two photodiodes 153 and 154. In the first pixel 151, the photodiodes 153 and 154 are connected in parallel, and one end is connected to the signal line 51 through the TFT 49. In the second pixel 152, on the other hand, an end of the photodiode 153 is connected to the signal line 51 through the TFT 49 as with the first pixel 151, while the photodiode 154 is directly connected to the signal line 51 without interposition of the TFT 49. In other words, the photodiode 154 of the second pixel 152 has the same structure as the detection pixel 65 of the above embodiments has.

From the first pixel 151, electric charge accumulated in the two photodiodes 153 and 154 is read out. From the second pixel 152, on the other hand, the electric charge accumulated only in the photodiode 153 is read out. Since the photodiode 154 of the second pixel 152 is used for the AEC and dose not contribute production of an X-ray image, the amount of the accumulated electric charge of the second pixel 152 is approximately a half of that of the first pixel 151, in a case where the same X-ray dose is applied to the photodiodes 153 and 154 of the same opening size. However, as compared with the above embodiments in which no pixel value is obtained from the position of the detection pixels 65, it is possible to prevent the deterioration in the image quality of the X-ray image. Also, the deterioration in the image quality can be further prevented by multiplying output of the second pixel 152 by a coefficient, which is calculated in advance based on the opening size of the photodiodes 153 and 154 and the like and corrects the pixel value of the second pixel 152 to a value corresponding to the pixel value of the first pixel 151 by multiplication. Thereby, it is possible to reduce an adverse effect on the image quality of the X-ray image, caused by using a part of the pixels of the FPD for the AEC.

Also, with taking advantage of the fact that an electric current flowing through the bias line, which supplies the bias voltage to each pixel 46, is in proportional to the electric charge produced in the pixel 46, the electric current flowing through the bias line connected to the specific pixel 46 may be monitored to detect the X-ray dose. In further another case, the X-ray dose may be detected based on a leak charge that leaks from the pixel 46 in a state where all the TFTs 49 are turned off. Furthermore, another detection sensor for the AEC that has different structure and independent output may be provided coplanarly to imaging surface 47, other than the pixels 46.

Comparing the integrated value of the dose detection signal with the threshold value by the AEC unit 62, an expected time for the accumulative dose of the X-rays to reach a target value may be calculated. In this case, the emission stop signal is transmitted to the source control device 11 after a lapse of the expected time, or the expected time is transmitted to the source control device 11. After a lapse of the expected time, the controller 42 shifts the operation of the FPD 45 from the accumulation operation to the readout operation.

Figure 18:
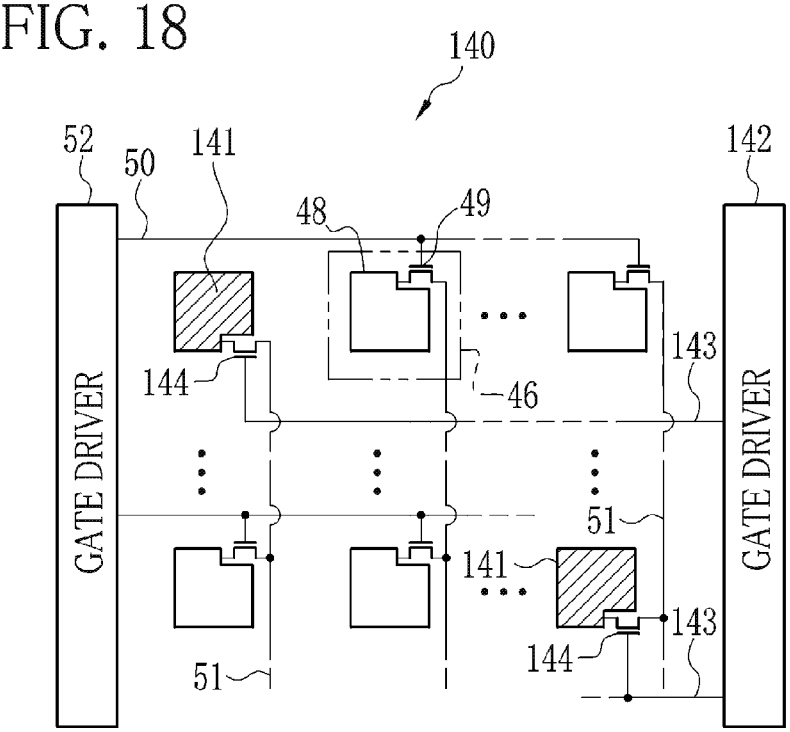
FIG. 18 is a diagram of an FPD of another embodiment.

In the case of using the FPD 140 of FIG. 18, which can read out the accumulated electric charge from the detection pixels 141 independently of from the normal pixels 46, when the expected time for the accumulative dose of the X-rays to reach the target value is calculated, the detection pixels 141 of the measurement area whose TFTs 144 were turned on periodically until then to provide the dose detection signals to the AEC unit 62 may be switched to the accumulation operation. The electric charge accumulated in the detection pixels 141 in this accumulation operation may be used for producing the X-ray image.

Figure 20:
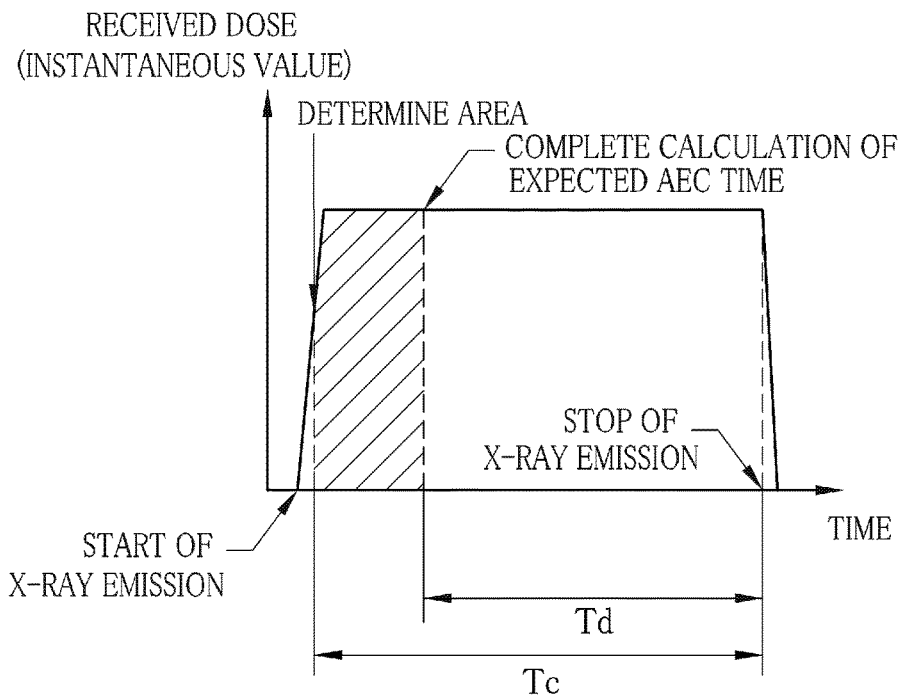
FIG. 20 is an explanatory view showing a state of shifting a detection pixel to an accumulation operation after calculating an expected time for an X-ray accumulative dose to reach a target value.

In this case, however, as shown by hatching in FIG. 20, only the electric charge produced during a time Td, which is after calculating the expected time and shifting to the accumulation operation, is reflected in a voltage signal outputted from the detection pixel 141 of the measurement area in the readout operation. The accumulative electric charge produced for the duration of time from the determination of each area until the calculation of the expected time is used for the AEC and not reflected in the X-ray image. Thus, a value of the detection pixel 141 is less by an amount of hatching than that of the normal pixel 46. Accordingly, the voltage signal outputted from the detection pixel 141 of the measurement area is multiplied by a ratio Tc/Td for correction. Wherein, Td represents an accumulation operation time of the detection pixels 141 of the measurement area, that is, a time from calculating the expected time and shifting to the accumulation operation until stopping the X-ray emission and starting the readout operation. Tc represents a time from determining each area until starting the readout operation. Note that, the other detection pixels 141 situated in the areas other than the measurement area shift to the accumulation operation immediately after determining each area. Thus, not only the detection pixels 141 of the areas other than the measurement area but also the detection pixels 141 of the measurement area can contribute to the production of the X-ray image, and minimize the deterioration in the image quality due to the provision of the detection pixels 141.

Note that, in contrast to each of the above embodiments, some X-ray imaging systems have no communication function between the source control device 11 and the electronic cassette 13. In this case, an emission start and/or stop detecting unit is provided instead of the AEC unit 62 to detect the start and/or the stop of the X-ray emission based on the dose detection signal. In detecting the start of the X-ray emission, when the imaging condition is set in the console 14, the FPD 45 is shifted from the reset operation to the accumulate operation and the detecting unit starts detecting the dose detection signal. An integrated value of the dose detection signal is compared with an emission start threshold value. When the integrated value has reached the emission start threshold value, it is judged that the X-ray emission has started. The FPD 45 continues the accumulation operation after the judgment of the start of the emission, and the dose detection signal is continuously monitored. When the integrated value comes to lower than an emission stop threshold value, it is judged that the X-ray emission has stopped, and the FPD 45 is shifted from the accumulation operation to the readout operation.

As is apparent from the above explanation, the basic structure of the emission start and/or stop detecting unit is the same as that of the AEC unit 62, though only the threshold values to be compared with the integrated value of the dose detection signal are different. However, the emission start and/or stop detecting unit does not have the measurement area determination unit 123. The emission start and/or stop detecting unit uses the dose detection signal of the detection pixel 65 that is determined to be situated in the directly exposed area by the object area determination unit 121 for judging the start and/or the stop of the X-ray emission. The directly exposed area receives more X-ray dose than the object area receives, and variation of the received dose per unit of time is larger in the directly exposed area than in the object area. Thus, it is possible to obtain in a short time the dose detection signal having an S/N that is adequate for judging the start and/or the stop of the X-ray emission. Thus, the precise and quick judgment is carried out.

Note that, instead of determining the directly exposed area using the object area determination unit 121, a maximum value of the dose detection signal may be used for judging the start and/or the stop of the X-ray emission. Not detecting the directly exposed area and the like facilitates shortening time required for the judgment.

In addition to using the dose detection signal for detecting the start or the stop of the X-ray emission and the AEC, a gain of the integration amplifier during the readout operation may be changed based on the dose detection signal. In this case, as shown in FIG. 21, a gain adjustable integration amplifier 160 is used instead of the integration amplifier 56.

Figure 21:
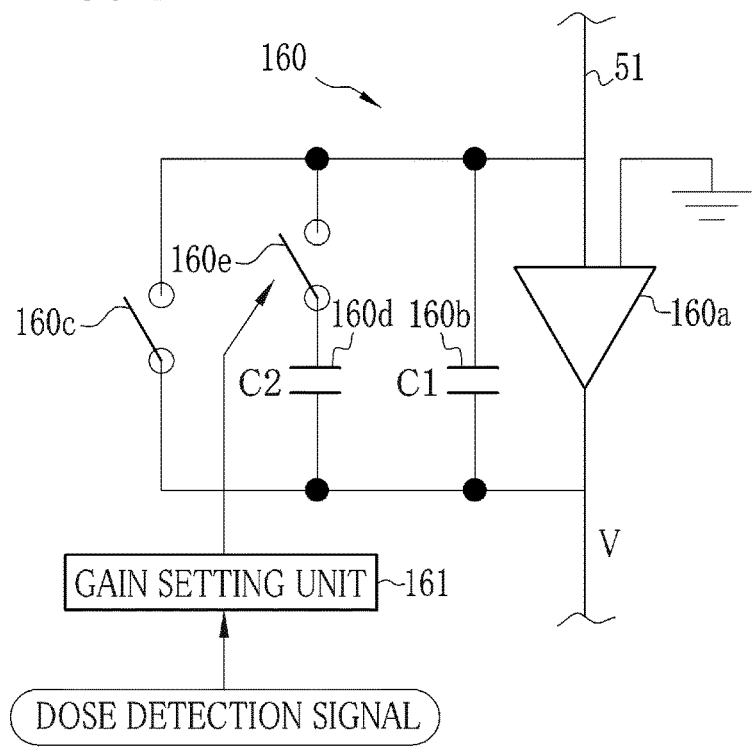
FIG. 21 is a diagram showing structure in the case of setting a gain of an integration amplifier during a readout operation.

In FIG. 21, the integration amplifier 160 has an operational amplifier 160a and a reset switch 160c, just as with the integration amplifier 56. Two capacitors 160c and 160d are connected between input and output terminals of the operational amplifier 160a. To the capacitor 160d, a gain change switch 160e is connected. When the gain change switch 160e is turned on, an output voltage signal V from the integration amplifier is $V=q/(C1+C2)$. When the gain change switch 160e is turned off, $V=q/C1$. Wherein, q represents accumulative electric charge. C1 and C2 represents capacitance of the capacitors 160b and 160d, respectively. By turning on and off the gain change switch 160e, the gain of the integration amplifier 160 is changed. Note that, an example of changing the gain in two stages by connecting the two capacitors is described above, but the gain is preferably changeable in two or more stages by connecting two or more capacitors or using a variable capacitor.

A gain setting unit 161 is provided in the FPD, in addition to the AEC unit 62 or the emission start and/or stop detecting unit. The gain setting unit 161 is actuated when the FPD starts the accumulation operation, to control the operation of the gain change switch 160e during the readout operation.

To the gain setting unit 161, the dose detection signal is periodically inputted from the signal processing circuit 55. In outputting the dose detection signal, the gain of the integration amplifier 160 is set at its minimum value in order to prevent saturation of the dose detection signal. In this example, the gain change switch 160e is turned on.

Just as with the AEC unit 62, the gain setting unit 161 integrates, for a predetermined number of times, a sum value, an average value, a maximum value, or a mean value of the dose detection signal from the detection pixel 65 situated in the measurement area determined by the measurement area determination unit 123. The integrated value is compared with a predetermined threshold value. In a case where the integrated value is larger than the threshold value, the gain setting unit 161 turns on the gain change switch 160e in the readout operation. On the other hand, when the accumulative received dose of a portion that is supposed to be the measurement area of the imaging surface 47 is low and the integrated value is the threshold value or less, the gain change switch 160e is turned off during the readout operation to increase the gain of the integration amplifier 160. More specifically, the gain of the integration amplifier 160 is set such that maximum and minimum values of the output voltage signal V of the measurement area coincide with maximum and minimum values of an A/D conversion range.

In the case of setting the accumulative X-ray dose at low, the width between the maximum and minimum values of the voltage signal V is narrower than the A/D conversion range. The X-ray image obtained in this case is an unclear image with conspicuous noise. However, setting the gain of the integration amplifier at a high level, when the accumulative received dose of the portion that is supposed to be the measurement area is low, allows obtainment of the X-ray image of high image quality with inconspicuous noise. Therefore, it is possible to reduce a level of the X-ray dose set in the X-ray source. As a result, a remarkable effect, that is, to reduce radiation exposure of the patient is obtained. Also, the X-ray emission may be early stopped on purpose by setting the emission stop threshold value of the AEC at a low level, and the gain of the integration amplifier may be set at a high level to make up a shortfall. The radiation exposure of the patient can be reduced also in this situation.

Note that, the gain of the integration amplifier 160 is changed in the above example. However, a gain variable amplifier may be provided other than the integration amplifier, and the change of the gain may be performed thereby.

The console 14 and the electronic cassette 13 are separate in each of the above embodiments, but the console 14 is not necessarily independent of the electronic cassette 13. The electronic cassette 13 may have the function of the console 14. In a like manner, the source control device 11 and the console 14 may be integrated into one unit. The present invention may be applied to a stand-mount type X-ray image detecting device, instead of or in addition to the electronic cassette being a portable X-ray image detecting device.

The present invention is applicable to an imaging system using another type of radiation such as γ-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging system including an x-ray or γ-ray radiation source for emitting x-ray or γ-ray radiation to an object, and an x-ray or γ-ray radiation image detecting device having an x-ray or γ-ray detection panel formed with an imaging surface for imaging a radiographic image of said object, said imaging surface having an array of a plurality of pixels each for accumulating electric charge in accordance with a received dose of said radiation emitted from said radiation source, said radiation imaging system comprising:
   a plurality of dose detection sensors disposed in said imaging surface, for detecting said received dose;
   an expected received dose obtainment unit for obtaining an expected received dose that is expected to be applied to a part of said imaging surface;
   an area determination unit for determining a measurement area out of said imaging surface based on a comparison result between said expected received dose and said received dose detected by said dose detection sensor, said measurement area being used in performing automatic exposure control that makes said radiation source stop emitting said radiation to control exposure of said radiographic image and said measurement area being set at a region of interest in making a diagnosis; and
   an automatic exposure control unit for performing said automatic exposure control based on a comparison result between an integrated value of said received dose detected by said dose detection sensor situated in said measurement area and a predetermined emission stop threshold value,
   wherein said area determination unit performs area determination after said radiation source starts emitting said radiation and said received dose comes to a constant value.

2. The radiation imaging system according to claim 1, wherein
   said expected received dose obtainment unit calculates a first expected received dose of a directly exposed area in which said radiation is directly applied to said imaging surface without passing through said object, based on a distance between said radiation source and said imaging surface of said radiation image detecting device and tube voltage and tube current applied to said radiation source; and
   said area determination unit determines said directly exposed area by a comparison result between said first expected received dose and said received dose detected by said dose detection sensor, and determines an object area to which said radiation is applied through said object based on said determined directly exposed area.

3. The radiation imaging system according to claim 2, wherein said expected received dose obtainment unit calculates said first expected received dose by using an area dose expression by a numerical dose determination (NDD) method.

4. The radiation imaging system according to claim 1, further comprising:
   an operation input unit for designating a body part to be imaged; and
   a memory unit for storing a second expected received dose that is expected to be received by said measurement area on a body part basis, wherein
   said expected received dose obtainment unit obtains from said memory unit said second expected received dose in accordance with said body part inputted by said operation input unit; and
   said area determination unit determines said measurement area from a comparison result between said second expected received dose and said received dose detected by said dose detection sensor.

5. The radiation imaging system according to claim 4, wherein said radiation image detecting device includes:
   a gain variable amplifier for amplifying an analog voltage signal that corresponds to electric charge from said pixel in a readout operation for reading out said radiographic image from said detection panel; and
   a gain setting unit for setting a gain of said amplifier during said readout operation, based on said received dose detected by said dose detection sensor situated in said measurement area in said automatic exposure control.

6. The radiation imaging system according to claim 1, wherein said area determination unit performs area determination by comparing with said expected received dose a typical value of said received doses detected by a plurality of said dose detection sensors contained in a block into which said imaging surface is divided.

7. The radiation imaging system according to claim 1, further comprising:
   a candidate area setting unit for setting a candidate area of said measurement area, said measurement area being set at the region of interest in making a diagnosis, wherein
   said area determination unit determines said measurement area out of said candidate area.

8. The radiation imaging system according to claim 1, further comprising:
   an irradiation field determination unit for determining said irradiation field, wherein
   said radiation source is provided with an irradiation field limiter for limiting an irradiation field that is irradiated with said radiation within said imaging surface; and
   said irradiation field determination unit determines said irradiation field in said imaging surface based on a collimator angle of said irradiation field limiter and a positional relation between said radiation source and said radiation image detecting device.

9. The radiation imaging system according to claim 8, wherein said irradiation field determination unit determines said irradiation field, and then said area determination unit determines said object area in said irradiation field and then determines said measurement area in said object area.

10. The radiation imaging system according to claim 8, further comprising:
    a candidate area setting unit for setting a candidate area of said measurement area, said measurement area being set at the region of interest in making a diagnosis, wherein
    said irradiation field determination unit determines said irradiation field out of said candidate area.

11. The radiation imaging system according to claim 1, wherein said automatic exposure control unit makes said radiation source stop emitting said radiation, as soon as said integrated value has reached said emission stop threshold value.

12. The radiation imaging system according to claim 1, wherein said automatic exposure control unit calculates an expected time required for said integrated value to reach said emission stop threshold value, and makes said radiation source stop emitting said radiation after a lapse of said calculated time.

13. The radiation imaging system according to claim 1, wherein said pixels include:

a normal pixel for accumulating signal charge by receiving said radiation and outputting said signal charge in response to an operation of a switching element; and a detection pixel directly connected to a signal line without interposition of said switching element, said detection pixel being used as said dose detection sensor.

14. The radiation imaging system according to claim 1, wherein said pixels include:
    a normal pixel for accumulating signal charge by receiving said radiation and outputting said signal charge in response to an operation of a switching element; and
    a detection pixel having a switching element that is driven independently of said normal pixel, said detection pixel being used as said dose detection sensor.

15. The radiation imaging system according to claim 1, carrying out continuous imaging in which said radiation source and said radiation image detecting device are relatively shifted to make an exposure of each of a plurality of divided imaging areas into which a longitudinal imaging area is divided, and a plurality of divided images corresponding to said divided imaging areas are merged to produce one longitudinal image.

16. The radiation imaging system according to claim 1, wherein said radiation image detecting device is an electronic cassette having said detection panel contained in a portable housing.

17. An operating method of a radiation imaging system including an x-ray or γ-ray radiation source for emitting x-ray or γ-ray radiation to an object;
    an x-ray or γ-ray radiation image detecting device having an x-ray or γ-ray detection panel formed with an imaging surface for imaging a radiographic image of said object, said imaging surface having an array of a plurality of pixels each for accumulating electric charge in accordance with a received dose of said radiation emitted from said radiation source; a plurality of dose detection sensors disposed in said imaging surface, for detecting said received dose; and an automatic exposure control unit for performing automatic exposure control by which emission of said radiation from said radiation source is stopped based on a comparison result between an integrated value of said received dose detected by said dose detection sensor and a predetermined emission stop threshold value in order to control exposure of said radiographic image, said operating method comprising:
    an expected received dose obtaining step for obtaining an expected received dose that is expected to be applied to a part of said imaging surface;
    an area determining step for determining a measurement area used in performing said automatic exposure control, out of said imaging surface based on a comparison result between said expected received dose and said received dose detected by said dose detection sensor, said measurement area being set at a region of interest in making a diagnosis; and
    an automatic exposure controlling step for performing said automatic exposure control by using said dose detection sensor situated in said measurement area,
    wherein said area determination step is performed after said radiation source starts emitting said radiation and said received dose comes to a constant value.

18. An x-ray or γ-ray radiation image detecting device comprising:
    an x-ray or γ-ray detection panel formed with an imaging surface for imaging a radiographic image of an object, said imaging surface having an array of a plurality of pixels each for accumulating electric charge in accordance with a received dose of x-ray or γ-ray radiation emitted from an x-ray or γ-ray radiation source;
    a plurality of dose detection sensors disposed in said imaging surface, for detecting said received dose;
    an expected received dose obtainment unit for obtaining an expected received dose that is expected to be applied to a part of said imaging surface;
    an area determination unit for determining a measurement area out of said imaging surface based on a comparison result between said expected received dose and said received dose detected by said dose detection sensor, said measurement area being used in performing automatic exposure control that makes said radiation source stop emitting said radiation to control exposure of said radiographic image and said measurement area being set at a region of interest in making a diagnosis; and
    an automatic exposure control unit for performing said automatic exposure control based on a comparison result between an integrated value of said received dose detected by said dose detection sensor situated in said measurement area and a predetermined emission stop threshold value,
    wherein said area determination unit performs area determination after said radiation source starts emitting said radiation and said received dose comes to a constant value.

* * * * *